(12) United States Patent
Shioga et al.

(10) Patent No.: US 11,797,734 B2
(45) Date of Patent: Oct. 24, 2023

(54) INFORMATION PROCESSING DEVICE, COMPUTER-READABLE RECORDING MEDIUM RECORDING MIXTURE PERFORMANCE OPTIMIZATION PROGRAM, AND MIXTURE PERFORMANCE OPTIMIZATION METHOD FOR SIMPLIFYING ENERGY FUNCTION FORMULA BY INCORPORATING CORRELATION FORMULA INTO ENERGY FUNCTION FORMULA

(71) Applicant: FUJITSU LIMITED, Kawasaki (JP)

(72) Inventors: Takeshi Shioga, Toshima (JP); Hideyuki Jippo, Atsugi (JP); Mari Ohfuchi, Hadano (JP)

(73) Assignee: FUJITSU LIMITED, Kawasaki (JP)

( * ) Notice: Subject to any disclaimer, the term of this patent is extended or adjusted under 35 U.S.C. 154(b) by 356 days.

(21) Appl. No.: 17/120,327

(22) Filed: Dec. 14, 2020

(65) Prior Publication Data

US 2021/0256185 A1 Aug. 19, 2021

(30) Foreign Application Priority Data

Feb. 17, 2020 (JP) .................................. 2020-024182

(51) Int. Cl.
*G06F 30/28* (2020.01)
*G06F 111/04* (2020.01)
*G06F 113/08* (2020.01)

(52) U.S. Cl.
CPC .......... *G06F 30/28* (2020.01); *G06F 2111/04* (2020.01); *G06F 2113/08* (2020.01)

(58) Field of Classification Search
CPC .. G06F 30/28; G06F 2111/04; G06F 2113/08; G06F 1/20; G06F 2200/201; G16C 60/00; G16C 20/30; C09K 5/10
See application file for complete search history.

(56) References Cited

U.S. PATENT DOCUMENTS

| 6,611,735 B1 | 8/2003 | Henly et al. |
| 2013/0008204 A1 | 1/2013 | Kim et al. |
| 2017/0338532 A1* | 11/2017 | Mott .................. H01M 10/659 |

FOREIGN PATENT DOCUMENTS

| EP | 0865890 A1 | 9/1998 |
| JP | H10-055348 A | 2/1998 |

(Continued)

OTHER PUBLICATIONS

Mohsen Hosseinzadeh et al., "Toward a predictive model for estimating viscosity of ternary mixtures containing ionic liquids," Journal of Molecular Liquids 200 (2014) 340-348 (Year: 2014).*

(Continued)

*Primary Examiner* — Steven W Crabb
(74) *Attorney, Agent, or Firm* — Fujitsu Patent Center

(57) ABSTRACT

An information processing device includes; a memory; and a processor coupled to the memory and configured to: optimize performance of a mixture of a plurality of substances; in an energy function formula for weighting each of a plurality of physical properties in the mixture and performing a calculation to optimize the performance of the mixture, collectively incorporate a plurality of the physical properties that has a relationship correlated with one characteristic among the plurality of the physical properties into the energy function formula as the one characteristic; and simplify the energy function formula.

11 Claims, 14 Drawing Sheets

(56) References Cited

FOREIGN PATENT DOCUMENTS

| JP | H10-152452 | A |   | 6/1998 |   |
|----|------------|---|---|--------|---|
| JP | 2001-192679 | A |   | 7/2001 |   |
| JP | 2012-057195 | A |   | 3/2012 |   |
| JP | 2013-540973 | A |   | 11/2013 |   |
| WO | WO-2014066938 | A1 | * | 5/2014 | .............. F24J 2/04 |

OTHER PUBLICATIONS

J. A. Klein et al., "Computer Aided Mixture Design With Specified Property Constraints," European Symposium on Computer Aided Process Engineering (Year: 1992).*

E. Khorshid et al., "Performance Investigation on New Refrigerant Mixture," 2011 Fourth International Conference on Modeling, Simulation and Applied Optimization, Kuala Lumpur, Malaysia (Year: 2011).*

Amin Hadidi "A novel approach for optimization of electrically serial two-stage thermoelectric refrigeration systems using chemical reaction optimization (CRO) algorithm," Energy 140 (Year: 2017).*

European Office Action dated Jun. 13, 2022 for corresponding European Patent Application No. 202137543, 8 pages.

Shioga, Takeshi et al., "Optimization of Thermophysical Properties for Mixed Refrigerants with Digital Annealer", The Proceedings of The Thermal Engineering Conference, 5 pages, Oct. 12-13, 2019, with English Abstract, Retrieved from the Internet:URL:http://dx.doi.org/10.1299/jsmeted.2019.0018, Extended European Search Report (EESR) dated Jun. 17, 2021 for corresponding European Patent Application No. 20213754.3, XP55807171A.

Hada, Subin et al., "Mixture formulation through multivariate statistical analysis of process data in property cluster space", Computers & Chemical Engineering, vol. 107, pp. 26-36, Jul. 8, 2017, XP85271153A.

Polizzi, Mark A. et al., "A framework for in-silico formulation design using multivariate latent variable regression methods", International Journal of Pharmaceutics, Elsevier, NL, vol. 418, No. 2, pp. 235-242, Apr. 26, 2011, XP28297481.

Tomba, Emanuele et al., "In-silico product formulation design through latent variable model inversion", Chemical Engineering Research and Design, vol. 92, No. 3, pp. 534-544, Sep. 2, 2013, XP55737833.

Karunanithi, Arunpraskash et al., "A New Decomposition-Based Computer-Aided Molecular/Mixture Design Methodology for the Design of Optimal Solvents and Solvent Mixtures", Industrial & Engineering Chemistry Research, vol. 44, No. 13, pp. 4785-4797, May 20, 2005, Retrieved from the Internet:URL:https://pubs.acs.org/doi/pdf/10.1021/ie049328h, XP55807342A.

Conte, Elisa et al., "Design of Formulated Products: A Systematic Methodology", AICHE Journal, vol. 57, No. 9, pp. 2431-2449, Oct. 7, 2010, XP55807351A.

Extended European Search Report dated Jun. 17, 2021 for corresponding European Patent Application No. 20213754.3, 10 pages.

Tamura, R. et al., "Formulation of variable selection problem in regression equation considering multicollinearity", Operations Research, vol. 63, No. 3, pp. 128-133, Mar. 2018, search date: Jul. 31, 2023 <URL:https://orsj.org/wp-content/corsj/or63-3/or63_3_128.pdf>, with Partial English Translation. Cited in JPOA dated Aug. 8, 2023 for corresponding Japanese Patent Application No. 2020-024182.

Japanese Office Action dated Aug. 8, 2023 for corresponding Japanese Patent Application No. 2020-024182, with English Translation, 11 pages.

* cited by examiner

INFORMATION PROCESSING DEVICE, COMPUTER-READABLE RECORDING MEDIUM RECORDING MIXTURE PERFORMANCE OPTIMIZATION PROGRAM, AND MIXTURE PERFORMANCE OPTIMIZATION METHOD FOR SIMPLIFYING ENERGY FUNCTION FORMULA BY INCORPORATING CORRELATION FORMULA INTO ENERGY FUNCTION FORMULA

CROSS-REFERENCE TO RELATED APPLICATION

This application is based upon and claims the benefit of priority of the prior Japanese Patent Application No. 2020-24182, filed on Feb. 17, 2020, the entire contents of which are incorporated herein by reference.

FIELD

The embodiments discussed herein are related to a mixture performance optimization device, a mixture performance optimization program, a mixture performance optimization method, and a mixed refrigerant.

BACKGROUND

Components such as central processing units (CPUs) in electronic equipment such as servers and network equipment sometimes generate heat and have a high temperature during the operation of the electronic equipment. If a high-heat-generating component such as a CPU generates heat to a temperature that exceeds the proper temperature, the high-heat-generating component can cause a variety of malfunctions, and therefore, in order to operate electronic equipment stably, it is preferable to appropriately cool the high-heat-generating component such as a CPU.

Japanese National Publication of International Patent Application No. 2013-540973 is disclosed as related art.

SUMMARY

According to an aspect of the embodiments, an information processing device includes; a memory; and a processor coupled to the memory and configured to: optimize performance of a mixture of a plurality of substances; in an energy function formula for weighting each of a plurality of physical properties in the mixture and performing a calculation to optimize the performance of the mixture, collectively incorporate a plurality of the physical properties that has a relationship correlated with one characteristic among the plurality of the physical properties into the energy function formula as the one characteristic; and simplify the energy function formula.

The object and advantages of the invention will be realized and attained by means of the elements and combinations particularly pointed out in the claims.

It is to be understood that both the foregoing general description and the following detailed description are exemplary and explanatory and are not restrictive of the invention.

DESCRIPTION OF EMBODIMENTS

Figure 1:
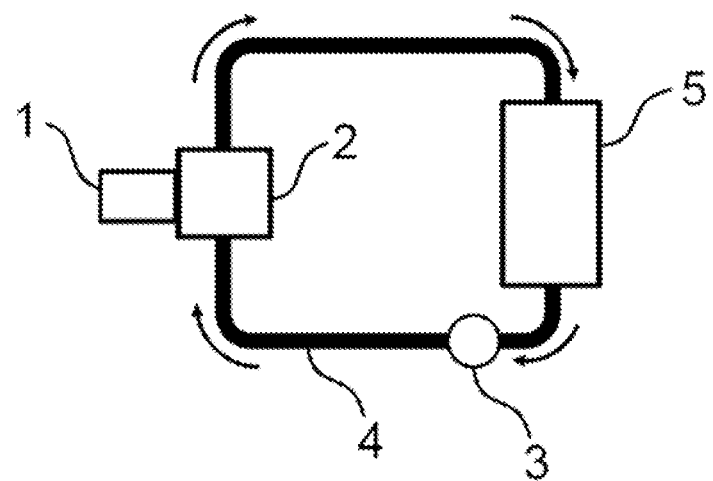
FIG. 1 is a diagram illustrating an exemplary configuration diagram of a liquid cooling system.

As a method of cooling a high-heat-generating component such as a CPU, there is a method using a liquid cooling system in which heat of the high-heat-generating component is transferred to a refrigerant and moved. Water is often used as the refrigerant used in the liquid cooling system.

However, since water has electrical conductivity, when water is used as the refrigerant, there is a risk that components of the electronic equipment would be short-circuited and destroyed, and serious accidents would occur in the electronic equipment and the entire system including the electronic equipment, if water leaks to the outside of the liquid cooling system.

For this reason, studies are underway on insulating refrigerants that do not have electrical conductivity. For the insulating refrigerants, a refrigerant (mixed refrigerant) formed from a mixture obtained by mixing a plurality of substances is used in some cases for the purpose of improving the cooling performance of the refrigerant.

Regarding the performance evaluation of the mixed refrigerant, a technique has been proposed in which an objective function is determined using a parameter of the nixed refrigerant obtained by the flash calculation (vapor-liquid equilibrium calculation), and this objective function is optimized by a genetic algorithm to evaluate the performance of the mixed refrigerant.

Furthermore, the problem of searching for an optimum combination of the types of substances to be mixed and the amount of each substance using the thermophysical properties of the mixed refrigerant as an index such that the cooling performance of the mixed refrigerant can be optimized may be deemed as a combinatorial optimization problem. The combinatorial optimization problem is a problem to work out an optimum combination from among a huge number of combinations in consideration of various conditions and constraints.

However, when the performance of a mixture of a plurality of substances is to be optimized by solving the combinatorial optimization problem as in the above example of the mixed refrigerant, there have been cases where optimum candidates for the mixture could not be sufficiently narrowed down when the number of physical properties (parameters) to be optimized is large.

In an aspect, a mixture performance optimization device, a mixture performance optimization program, and a mixture performance optimization method capable of optimizing the performance of a mixture in terms not only of the calculation result but also of the actual performance, even when an energy function formula for weighting each of a plurality of physical properties in the mixture and performing a calculation to optimize the performance of the mixture contains many physical properties, and a mixed refrigerant with optimized performance may be provided.

(Mixture Performance Optimization Device)

A mixture performance optimization device disclosed in the present application is a device that optimizes the performance of a mixture of a plurality of substances. The mixture performance optimization device disclosed in the present application preferably includes an energy function formula simplification unit and a performance optimization unit, and further includes another unit (mechanism), depending on the situation.

Prior to explaining the details of the technique disclosed in the present application, a problem and the like of prior art will be described by taking as an example a case where the performance of a mixed refrigerant is optimized.

As described earlier, as a method of cooling a high-heat-generating component such as a CPU of electronic equipment, for example, a method using a liquid cooling system in which heat of the high-heat-generating component is transferred to a refrigerant and moved can be mentioned. Here, FIG. 1 illustrates an exemplary configuration diagram of a cooling system using the liquid cooling system.

In the example illustrated in FIG. 1, a high-heat-generating component 1 is in contact with a heat receiver 2, and heat generated by the high-heat-generating component 1 is transferred to a refrigerant flowing through the heat receiver 2. When a pump 3 is driven, the refrigerant circulates in a piping 4 in the directions of the arrows. The refrigerant heated at the heat receiver 2 is carried to a heat radiator 5, and the temperature of the refrigerant lowers due to heat exchange between a heat radiation fin of the heat radiator 5 and the air. Thereafter, the refrigerant flows into the heat receiver 2 again and takes away heat generated by the high-heat-generating component 1, such that the high-heat-generating component 1 can be lowered in temperature and cooled.

Here, the cooling performance of the liquid cooling system is affected by the thermophysical properties of the refrigerant being used. Examples of the thermophysical properties of the refrigerant used in the liquid cooling system include, for example, thermal conductivity, specific heat, viscosity, vapor pressure, boiling point, surface tension, latent heat of vaporization, and the like. Furthermore, as the physical properties of the refrigerant used in the liquid cooling system, for example, physical properties such as combustibility, flammability, ignitability, toxicity, and environmental impact are considered in some cases, in addition to the above-mentioned thermophysical properties.

As mentioned above, since water, which is often used as a refrigerant in the liquid cooling system, has electrical conductivity, if water leaks to the outside of a cooling system, there is a risk that components of electronic equipment would be short-circuited and destroyed, and serious accidents would occur in the entire system including the electronic equipment.

For this reason, studies are underway on a refrigerant containing insulating fluorine that has no electrical conductivity (fluorine-based refrigerant).

However, while fluorine-based refrigerants have insulating properties, the thermophysical properties (cooling performance) of fluorine-based refrigerants are often inferior to the thermophysical properties of water. For example, in a normal fluorine-based refrigerant, the thermal conductivity is about $\frac{1}{10}$ of that of water, and the specific heat is around $\frac{1}{4}$ of that of water. Accordingly, the performance of the liquid cooling system using the fluorine-based refrigerant is lower than the case using water.

Thus, in order to improve the cooling performance when the insulating fluorine-based refrigerant is used, attempts have been made to improve the thermophysical properties as a refrigerant, such as the thermal conductivity, by mixing a plurality of other materials (for example, an organic solvent) based on the fluorine-based refrigerant. A refrigerant thus formed from a mixture obtained by mixing a plurality of substances is referred to as a mixed refrigerant.

When a mixed refrigerant based on a fluorine-based refrigerant is developed, it is sometimes desired to optimize a plurality of thermophysical properties of the mixed refrigerant and determine materials (substances) to be mixed and the mixing ratio of these materials such that the cooling performance of the mixed refrigerant is improved.

In this manner, the problem of searching for an optimum combination of materials (substances) to be mixed and the mixing ratio of these materials using the thermophysical properties of the mixed refrigerant as an index such that the cooling performance of the mixed refrigerant can be optimized may be deemed as a combinatorial optimization problem. A mixed refrigerant in which the materials (substances) to be mixed and the mixing ratio of these materials are selected by solving the combinatorial optimization problem has optimized thermophysical properties desired as a refrigerant and is given excellent cooling performance.

In the combinatorial optimization problem, as the number of factors to be considered increases, the number of combinations of factors increases exponentially and hugely. Accordingly, in a conventional calculation approach in which processes are performed sequentially, it is difficult to solve the combinatorial optimization problem in a practical time when the number of factors to be considered is large.

Thus, as a technique capable of solving the combinatorial optimization problem at high speed, a technique of performing calculation by an annealing method (annealing) using an annealing machine or the like has been proposed. As the approach to solve the combinatorial optimization problem by the annealing method, for example, an approach using an "energy function", which is a function based on conditions and constraints in the combinatorial optimization problem, can be mentioned. Note that the energy function is referred to as an objective function, a cost function, a Hamiltonian, or the like in some cases.

The energy function (energy function formula) is a function that takes the minimum value when variables (parameters) in the energy function have an optimum combination in the combinatorial optimization problem. Accordingly, the solution of the combinatorial optimization problem can be located by searching for a combination of variables with which the energy function has the minimum value.

Figure 2:
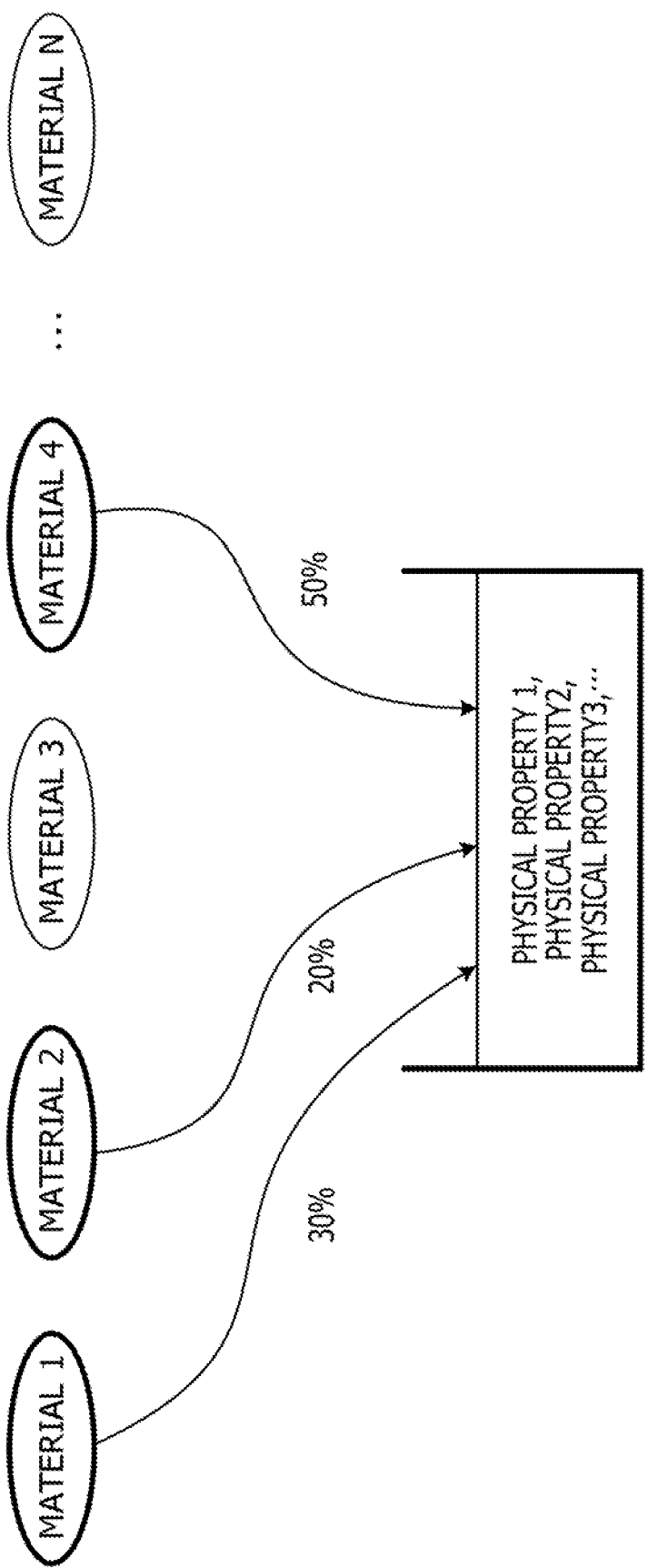
FIG. 2 is a diagram illustrating an example of how a combination of materials is chosen when a plurality of materials is mixed to formulate a mixture.

Here, in the combinatorial optimization problem to work out an optimum combination of materials (substances) to be mixed and the mixing ratio of these materials using the thermophysical properties of the mixed refrigerant as an index, for example, an energy function formula in which each thermophysical property is defined as a parameter can be used. As illustrated in FIG. 2, when a predetermined number (three in the example in FIG. 2) of materials are mixed from among materials 1 to N at a predetermined mixing ratio, the energy function formula is, for example, given as the following Formula.

$$E = \alpha \cdot [\text{Physical Property 1}] + \beta \cdot [\text{Physical Property 2}] + \gamma \cdot [\text{Physical Property 3}] + \ldots + \text{Constraint Term}$$

In the Formula, E denotes the energy function formula, and $\alpha$, $\beta$, and $\gamma$ denote weighting coefficients for the respective physical properties. Note that the constraint term is a term representing a constraint such as the number of selected materials (substances) in the energy function formula.

Furthermore, in the above energy function formula, [Physical Property 1] to [Physical Property N] are physical property values regarded as the goals of design of the mixed refrigerant, which are thermophysical properties desired to be optimized in order to maximize the cooling performance of the mixed refrigerant, and for example, the physical property values of the thermal conductivity, specific heat, and the like can be employed. Each physical property value in the above energy function formula is given a weighting coefficient, and by solving the combinatorial optimization problem while changing the weighting of each physical property (coefficients $\alpha$, $\beta$, $\gamma$, . . . ), setting as to which physical property value is emphasized (allocated with a larger weight) is allowed. Accordingly, by rightly setting each weighting coefficient as appropriate and solving the combinatorial optimization problem, it is deemed that the physical properties desired as a refrigerant are optimized, and the materials of the mixed refrigerant having excellent cooling performance and the mixing percentage between these materials (composition of the mixed refrigerant) can be located.

However, in the above method, for example, when there are many types of physical properties to be optimized, it is sometimes difficult to optimize all the physical properties. To give an example, in the above method, for example, when the number of physical properties to be optimized is large and the number of parameters of the energy function formula in which each physical property is defined as a parameter is large, it is difficult in some cases to optimize all the parameters of this energy function formula. This means that, if the number of parameters of the energy function formula is large, it is difficult to specify weighting coefficients that can sufficiently optimize all of these parameters, and even if a combination gives the minimum value to the energy function formula, there is a case where, in reality, the combination is not suitable as a mixed refrigerant. Accordingly, in the prior art, even if a combination of substances gives the minimum value to the energy function formula (is optimized) in terms of the calculation result, the combination is sometimes an inadequate combination that has not been optimized in terms of the performance in reality (actual performance) as a mixture in consideration of the usage and the like of the mixture.

For example, when the performance of the mixed refrigerant is optimized, in a case where five physical properties, namely, the thermal conductivity, specific heat, flash point, viscosity, and electroconductivity as the physical properties of the mixed refrigerant are employed as parameters of the energy function formula, a mixed refrigerant in which these physical properties are optimized sometimes may not be specified. In this example, due to the large number of physical properties to be optimized, a combination in which a specified physical property is excellent but other physical properties are not suitable for practical use is obtained as the calculation result of the combinatorial optimization problem in some cases.

For example, there is a case where a mixed refrigerant that is deemed to have high thermal conductivity and high heat transport performance, but has very high viscosity and has difficulty in flowing in a piping of the cooling system, and moreover, that has high electroconductivity, has electrical conductivity, and does not have insulating properties is specified as an optimum mixed refrigerant. Furthermore, even if the weighting coefficient for a parameter of the energy function formula is changed and the search for a high-performance mixed refrigerant is repeated, it is difficult to sufficiently narrow down optimum candidates for the mixture because the number of physical properties to be optimized is large.

As described above, in the prior art, when the performance of a mixture such as a mixed refrigerant is optimized, in a case where the number of physical properties to be optimized is large (the number of parameters of the energy function formula is large), it has been difficult to optimize the energy function formula in terms not only of the calculation result but also of the actual performance, and optimum candidates for the mixture may not be sufficiently narrowed down. Accordingly, in the prior art, even if a combination gives the minimum value to the energy function formula (is optimized) in terms of the calculation result, the combination has been sometimes a non-optimum inadequate combination in terms of the performance in reality (actual performance) as a mixture in consideration of the usage and the like of the mixture.

In view of this, the present inventors have diligently and continually studied on a device and the like capable of optimizing the performance of a mixture in terms not only of the calculation result but also of the actual performance, even when an energy function formula for performing a calculation to optimize the performance of the mixture contains many physical properties, and have obtained the following findings.

Accordingly, the present inventors have found that, in an energy function formula for weighting each of a plurality of physical properties in a mixture and performing a calculation to optimize the performance of the mixture, by collectively incorporating a plurality of the physical properties that has a relationship correlated with one characteristic among the plurality of the physical properties into the energy function formula as the one characteristic, and simplifying the energy function formula, the performance of the mixture may be optimized in terms not only of the calculation result but also of the actual performance, even when the energy function formula contains many physical properties. The technique disclosed in the present application is based on these findings.

Here, in an example of the technique disclosed in the present application, the performance of the mixture is optimized based on an energy function formula for weighting each of a plurality of physical properties in the mixture and performing a calculation to optimize the performance of the mixture. Moreover, in an example of the technique disclosed in the present application, in the energy function formula, a plurality of physical properties that has a relationship correlated with one characteristic among a plurality of physical properties is collectively incorporated into the energy function formula as the one characteristic, and the energy function formula is simplified.

As described above, in an example of the technique disclosed in the present application, for example, by collectively incorporating a plurality of physical properties that has a relationship correlated with one characteristic among a plurality of physical properties into an energy function formula as the one characteristic, the number of parameters contained in the energy function formula may be decreased. Accordingly, in an example of the technique disclosed in the present application, even when the original energy function formula contains many physical properties, the number of parameters contained in the energy function formula may be decreased and the energy function formula may be simplified, such that each parameter of the energy function formula may be optimized. This means that, since an example of the technique disclosed in the present application may decrease the number of parameters contained in the energy function formula, an appropriate weighting coefficient may be specified individually for all of the parameters, and the performance of the mixture may be optimized in terms not only of the calculation result but also of the actual performance.

Here, the simplification of the energy function formula in an example of the technique disclosed in the present application as described above will be described in more detail.

In an example of the technique disclosed in the present application, for example, an energy function formula as indicated by the following Formula can be used as described above.

$E = \alpha \cdot [\text{Physical Property 1}] + \beta \cdot [\text{Physical Property 2}] + \gamma \cdot [\text{Physical Property 3}] + \ldots + \text{Constraint Term}$ In an example of the technique disclosed in the present application, for example, a plurality of physical properties is collected into one characteristic, using a correlation formula as indicated by the following Formula.

$[\text{Characteristic 1}] = \alpha_1 \cdot [\text{Physical Property 1}] + \beta_1 \cdot [\text{Physical Property 2}]$ Here, $\alpha_1$ and $\beta_1$ denote weighting coefficients for the respective physical properties. Furthermore, $\alpha_1$ and $\beta_1$ can be worked out based on a correlation relationship between the characteristic 1 and the physical properties 1 and 2.

Then, in an example of the technique disclosed in the present application, for example, the energy function formula is simplified by incorporating the above correlation formula into the above energy function formula. For example, in an example of the technique disclosed in the present application, for example, by incorporating the above correlation formula into the above energy function formula, the energy function formula is transformed into the following Formula and the energy function formula is simplified.

$E = \delta \cdot [\text{Characteristic 1}] + \gamma \cdot [\text{Physical Property 3}] + \ldots + \text{Constraint Term}$ Here, $\delta$ denotes a coefficient that means a weighting parameter for the characteristic 1.

In the above simplified energy function formula, the physical properties 1 and 2 are collectively incorporated as the characteristic 1, and the number of parameters contained in the energy function formula is decreased. Accordingly, an appropriate weighting coefficient may be specified individually for all of the parameters in the above simplified energy function formula, and the performance of the mixture may be optimized in terms not only of the calculation result but also of the actual performance.

Here, a more specific example of the technique disclosed in the present application will be described.

For example, as in the above example, a case where, when the performance of a mixed refrigerant as a mixture is optimized, five physical properties, namely, the thermal conductivity, specific heat, flash point, viscosity, and electroconductivity as the physical properties of the mixed refrigerant are employed as parameters of the energy function formula will be examined.

In the above example, the cooling performance of the mixed refrigerant (the ability of the refrigerant to carry heat) is affected by the ease of heat transfer in the mixed refrigerant, and the ease of heat transfer can be represented using, for example, the thermal conductivity and the specific heat (or heat capacity) of the mixed refrigerant. Furthermore, when examined from another aspect, the cooling performance in the cooling system can also be represented using thermal resistance, which represents the difficulty of heat transfer. Accordingly, it can be deemed that the thermal conductivity and the specific heat of the mixed refrigerant have a relationship correlated with the thermal resistance in the cooling system.

Therefore, in an example of the technique disclosed in the present application, by collectively incorporating the thermal conductivity and the specific heat, which have a relationship correlated with the thermal resistance, among a plurality of physical properties of the mixed refrigerant into the energy function formula as one characteristic, which is the thermal resistance, the energy function formula may be simplified. This means that, in an example of the technique disclosed in the present application, by collectively incorporating the two physical properties of the mixed refrigerant, namely, the thermal conductivity and the specific heat, into the energy function formula as one characteristic, which is the thermal resistance, the number of parameters contained in the energy function formula may be decreased and the energy function formula may be simplified.

Furthermore, in an example of the technique disclosed in the present application, when a plurality of physical properties such as the thermal conductivity and the specific heat are collected into one characteristic, for example, a correlation formula relating to the plurality of physical properties may be worked out, and the plurality of physical properties may be replaced with one characteristic by the worked-out correlation formula. In this case, for example, a plurality of mixed refrigerant candidates is chosen using the prior art or the like, and the chosen mixed refrigerant candidates are subjected to a thermal fluid simulation or an experiment to work out a correlation relationship between the thermal conductivity and specific heat, and the thermal resistance in the mixed refrigerant candidates. In this example, for example, based on the worked-out correlation relationship, a correlation formula capable of representing the thermal resistance may be obtained with the thermal conductivity and the specific heat as parameters.

In an example of the technique disclosed in the present application, a plurality of physical properties may be optimized at the same time (comprehensively) by optimizing the energy function formula including the correlation formula in which the plurality of physical properties is collected into one characteristic. This means that, in an example of the technique disclosed in the present application, by applying the above correlation formula to the energy function formula, the thermal conductivity and the specific heat in the energy function formula may be collected into one characteristic as the thermal resistance, and the number of parameters (the number of physical properties) in the energy function formula may be decreased to simplify the energy function formula.

In the above-mentioned example of the mixed refrigerant, by using an example of the technique disclosed in the present application, composition of a mixed refrigerant may be specified in which, for example, the thermal resistance is low and the performance to transport heat (cooling performance) is high, while the electroconductivity is low and the insulating property is provided, and moreover, the flash point and the viscosity also fall within a preferable range as the refrigerant.

Note that the mixed refrigerant has been described up to this point as an example of the mixture for which the performance is to be optimized, but the technique disclosed in the present application is not restricted to putting the mixed refrigerant as a target.

As described above, in an example of the technique disclosed in the present application, by collectively incorporating a plurality of physical properties that has a relationship correlated with one characteristic among a plurality of physical properties into an energy function formula as the one characteristic, the number of parameters contained in the energy function formula may be decreased. Accordingly, in an example of the technique disclosed in the present application, an appropriate weighting coefficient may be set individually for all of the parameters, and it becomes easier to optimize each physical property in the energy function formula. This means that, in an example of the technique disclosed in the present application, since it is easy to optimize each physical property in the energy function formula, when the energy function formula is minimized, each physical property may be optimized, and a mixture that has been exactly optimized in terms not only of the calculation result but also of the actual performance may be specified.

Therefore, in an example of the technique disclosed in the present application, even when the energy function formula contains many physical properties, the performance of the mixture may be optimized in terms not only of the calculation result but also of the actual performance.

In the following, an example of the technique disclosed in the present application will be described with reference to the drawings. Note that, in the mixture performance optimization device as an example of the technique disclosed in the present application, processes (operations) such as the simplification of the energy function formula may be performed by, for example, the energy function formula simplification unit included in the mixture performance optimization device.

<Energy Function Formula Simplification Unit>

In an example of the technique disclosed in the present application, the energy function formula simplification unit optimizes the performance of the mixture based on an energy function formula for weighting each of a plurality of physical properties in the mixture and performing a calculation to optimize the performance of the mixture. Moreover, in an example of the technique disclosed in the present application, in the energy function formula, the energy function formula simplification unit collectively incorporates a plurality of physical properties that has a relationship correlated with one characteristic among a plurality of physical properties into the energy function formula as the one characteristic, and simplifies the energy function formula.

«Mixture»

The mixture for which the performance is to be optimized in the technique disclosed in the present application is not particularly limited as long as a mixture of a plurality of substances is employed, and can be appropriately selected depending on the intended purpose. This means that, in the technique disclosed in the present application, there is no particular limitation as long as the employed mixture is a mixture whose various performances and attributes can vary by changing the types and amounts of the substances to be mixed, and the mixture can be appropriately selected depending on the intended purpose.

Furthermore, in the technique disclosed in the present application, the substance (material) to be mixed into the mixture is not particularly limited, and can be appropriately selected depending on the intended purpose. In addition, the number of types of substances to be mixed into the mixture is not particularly limited as long as a plurality of (two or more) types is employed, and can be appropriately selected depending on the intended purpose.

In an example of the technique disclosed in the present application, it is preferable that the substance (material) to be mixed into the mixture be selected according to the type of the mixture, for example, from a database in which physical properties and the like of a large number of substances are recorded.

Moreover, in the technique disclosed in the present application, the performance of the mixture to be optimized is not particularly limited, and can be appropriately selected depending on the intended purpose. The performance of the mixture to be optimized by the technique disclosed in the present application can be selected according to the type of the mixture, for example, depending on a performance desired for the mixture.

Examples of the mixture for which the performance is to be optimized in the technique disclosed in the present application include, for example, a refrigerant, a cleaning agent, and food.

The refrigerant is not particularly limited as long as a refrigerant (mixed refrigerant) in which a plurality of substances (materials) is mixed is employed, and can be appropriately selected depending on the intended purpose; the refrigerant may be a gas at room temperature, or the refrigerant may be a liquid at room temperature.

Examples of the physical properties of the mixed refrigerant include, for example, the thermal resistance, thermal conductivity, specific heat, viscosity, vapor pressure, boiling point, surface tension, latent heat of vaporization, combustibility, flammability, ignitability, toxicity, energy efficiency, environmental impact, and the like. The energy efficiency can be represented using, for example, a coefficient of performance (COP). Furthermore, examples of environmental impacts include, for example, the global warming potential (GWP), the ozone-depleting potential (ODP), and the like.

Here, in the technique disclosed in the present application, among multiple physical properties in the mixture, a collection of a plurality of physical properties that has a relationship correlated with one physical property is sometimes referred to as "characteristic".

In the mixed refrigerant, among the above multiple examples of physical properties, for example, by assuming that the thermal conductivity and the specific heat have a relationship correlated with the thermal resistance, the two physical properties, namely, the thermal conductivity and the specific heat, can be collectively treated as one characteristic, which is the thermal resistance.

Furthermore, in the mixed refrigerant, among the above multiple examples of physical properties, for example, by assuming that the flash point and the specific gravity have a relationship correlated with the combustibility (combustion rate), the two physical properties, namely, the flash point and the specific gravity, can be collectively treated as one characteristic, which is the combustibility (combustion rate).

Moreover, in the mixed refrigerant, among the above multiple examples of physical properties, for example, by assuming that the latent heat of vaporization and the specific heat have a relationship correlated with the energy efficiency (COP), the two physical properties, namely, the latent heat of vaporization and the specific heat, can be collectively treated as one characteristic, which is the energy efficiency (COP).

As the mixed refrigerant, for example, one containing a fluorine compound is preferable. The fluorine compound contained in the mixed refrigerant is not particularly limited, and can be appropriately selected depending on the intended purpose. However, hydrofluoroolefin (HFO) is preferably contained because of its insulating property and low global warming potential (GWP).

The cleaning agent is not particularly limited as long as a cleaning agent in which a plurality of substances (materials) is mixed is employed, and can be appropriately selected depending on the intended purpose. Examples of the cleaning agent include, for example, water-based cleaning agents, semi-water-based cleaning agents, hydrocarbon-based cleaning agents, alcohol-based cleaning agents, chlorine-based cleaning agents, fluorine-based cleaning agents, and bromine-based cleaning agents.

The physical properties of the cleaning agent are not particularly limited, and can be appropriately selected depending on the intended purpose. Examples of the physical properties of the cleaning agent include, for example, the specific heat, viscosity, surface tension, latent heat of vaporization, combustibility, flammability, toxicity, hydrogen ion index (pH), evaporation rate, permeability, detergency for specified targets, and storage stability.

In the technique disclosed in the present application, the energy function formula may be simplified by collecting a plurality of physical properties appropriately selected according to the intended purpose from among the above physical properties and the like, into one characteristic.

The food is not particularly limited as long as a food in which a plurality of substances (materials) is mixed is employed, and can be appropriately selected depending on the intended purpose. Examples of the food include, for example, coffee. When the mixture to be optimized is coffee, in an example of the technique disclosed in the present application, for example, the type of coffee beans used as a raw material for the coffee and the amount of the coffee beans are worked out. This means that, in an example of the technique disclosed in the present application, an appropriate blending ratio of coffee beans in so-called blended coffee may be worked out.

The physical properties (features of tastes) of coffee are not particularly limited, and may be appropriately selected depending on the intended purpose. Examples of physical properties of coffee include aroma, sourness, bitterness, and richness.

In the technique disclosed in the present application, the energy function formula may be simplified by collecting a plurality of physical properties appropriately selected according to the intended purpose from among the above physical properties (features) and the like, into one characteristic.

«Energy Function Formula»

In an example of the technique disclosed in the present application, the performance of the mixture is optimized based on an energy function formula for weighting each of a plurality of physical properties in the mixture and performing a calculation to optimize the performance of the mixture.

Here, the energy function formula can be appropriately selected depending on the physical properties of the mixture, constraints on selecting a substance to be mixed into the mixture, and the like. As the energy function formula, for example, a function that takes the minimum value when an optimum combination of substances in the mixture is given, using the values of physical properties in the mixture as variables can be used. Accordingly, the performance of the mixture can be optimized by working out a combination of variables with which the energy function formula has the minimum value.

In an example of the technique disclosed in the present application, the energy function formula represented by the following Formula is preferable.

$$E = \alpha \cdot [\text{Physical Property 1}] + \beta \cdot [\text{Physical Property 2}] + \gamma \cdot [\text{Physical Property 3}] + \ldots + \text{Constraint Term}$$

In the Formula, E denotes the energy function formula, and $\alpha$, $\beta$, and $\gamma$ denote weighting coefficients for the respective physical properties. Note that the constraint term is a term representing a constraint such as the number of selected materials (substances) in the energy function formula. Furthermore, " . . . " in the above energy function formula means that a physical property other than the physical properties 1, 2, and 3, and a weighting coefficient other than $\alpha$, $\beta$, and $\gamma$ may be appropriately included.

Here, physical properties (physical property values) such as the physical properties 1 to 3 in the above energy function formula mean physical properties (mixed physical properties) in a mixture. The approach to work out the physical properties (mixed physical properties) of the mixture is not particularly limited, and can be appropriately selected depending on the intended purpose. As the approach to work out the physical properties of the mixture, an approach to work out the physical properties based on the physical properties of each substance (for example, a compound) in the mixture can be mentioned.

The approach to work out the physical properties of the mixture based on the physical properties of each substance in the mixture is not particularly limited, and can be appropriately selected depending on the types and attributes of the physical properties to be worked out. Furthermore, for the physical properties of each substance, literature values, measured values (values obtained by actually conducting experiments), values computed based on physical property simulations, and the like can be used.

As the approach to work out the physical properties of the mixture based on the physical properties of each substance in the mixture, for example, an approach using a value obtained by weighting and averaging the physical property values of multiple substances based on the molar concentration in the mixture of each substance to be mixed can be mentioned.

Regarding the case of using this approach, a case where, when the specific heat of a mixture is worked out (estimated), 50 mol of a substance A, 30 mol of a substance B, and 20 mol of a substance C are contained in 100 mol of the mixture is explained as an example. In this example, it is assumed that the specific heat of the substance A is 2000 J/(kg·K), the specific heat of the substance B is 4000 J/(kg·K), and the specific heat of the substance C is 1000 J/(kg·K). At this time, when the specific heat of the mixture is worked out based on the molar concentration of each substance using the specific heat of each of these substances, for example, the following Formula is given.

Specific Heat of Mixture=2000×(50/100)+4000×(30/100)+1000×(20/100)=2400 J/(kg·K)

In this manner, in an example of the technique disclosed in the present application, for example, a value obtained by weighting and averaging the physical property values of multiple substances based on the molar concentration in the mixture of each substance to be mixed can be taken as the physical properties of the mixture.

Furthermore, the approach to work out the physical properties of the mixture based on the physical properties of each substance in the mixture is not limited to the above approach, and for example, an approach of estimating the physical properties of the mixture by a theoretical or empirical physical property estimation formula can also be used.

As the theoretical or empirical physical property estimation formula, a known one can be appropriately selected and used, and for example, a formula disclosed in documents such as "Prediction Method for Physical Properties (OHE, Shuzo; Data Book Shuppansha)", and the like can be used. Specific examples and the like of the physical property estimation formula will be described later.

In addition, the constraint term in the above energy function formula preferably includes the following four constraints.

The constraint that the number of types of a plurality of substances to be mixed into the mixture is a predetermined number The constraint that the total mixing percentage between a plurality of substances in the mixture is 100%

The constraint that the same substance is not selected a plurality of times as a plurality of substances to be mixed into the mixture The constraint that the mixture contains a predetermined substance Here, first, "the constraint that the number of types of a plurality of substances to be mixed into the mixture is a predetermined number" among the above four constraints will be described.

When the performance of a mixture is optimized, the number of substances to be mixed is sometimes preset to search for a substance to be mixed into the mixture. In such a case, by imposing the above-mentioned "constraint that the number of types of a plurality of substances to be mixed into the mixture is a predetermined number", a search may be made by narrowing down to a mixture in which the predetermined number, which has been preset, of substances are mixed.

Furthermore, "the constraint that the number of types of a plurality of substances to be mixed into the mixture is a predetermined number" can be employed as, for example, a penalty term to raise the value of the energy function formula when a combination has the number of types of substances to be mixed into the mixture that is not the predetermined number.

Next, "the constraint that the total mixing percentage between a plurality of substances in the mixture is 100%" among the above four constraints will be described.

When a combination of substances in a mixture of a plurality of substances is searched for, the total mixing percentage between (contained quantities of) multiple substances to the total amount of the mixture is usually 100%. Accordingly, by imposing the above-mentioned "constraint that the total mixing percentage between a plurality of substances in the mixture is 100%", a search may be made by narrowing down such that the total mixing percentage between a plurality of substances matches 100%.

Furthermore, "the constraint that the total mixing percentage between a plurality of substances in the mixture is 100%" can be employed as, for example, a penalty term to raise the value of the energy function formula when a combination has a total mixing percentage between a plurality of substances in the mixture that is not 100%.

Subsequently, "the constraint that the same substance is not selected a plurality of times as a plurality of substances to be mixed into the mixture" among the above four constraints will be described.

When a combination of substances in a mixture of a plurality of substances is searched for, there is a case where a combination of diverse substances may not be located from among combinations in which the same substance is selected a plurality of times. Accordingly, by imposing the above-mentioned "constraint that the same substance is not selected a plurality of times as a plurality of substances to be mixed into the mixture", a search may be made by narrowing down to a mixture formed by a combination of substances different from each other.

Furthermore, "the constraint that the same substance is not selected a plurality of times as a plurality of substances to be mixed into the mixture" can be employed as, for example, a penalty term to raise the value of the energy function formula when a combination has the same substance that is selected a plurality of times as a plurality of substances to be mixed into the mixture.

Following the above, "the constraint that the mixture contains a predetermined substance" among the above four constraints will be described.

When a combination of substances in a mixture of a plurality of substances is searched for, there is a case where a base substance of the mixture is preset, and substances to be mixed into the mixture are searched for such that the base substance is included. Accordingly, by imposing the above-mentioned "constraint that the mixture contains a predetermined substance", a search may be made by narrowing down to a mixture containing the preset base substance.

Furthermore, "the constraint that the mixture contains a predetermined substance" can be employed as, for example, a penalty term to raise the value of the energy function formula when the mixture has a combination that does not contain the predetermined substance.

«Simplification of Energy Function Formula»

In an example of the technique disclosed in the present application, in the energy function formula, a plurality of physical properties that has a relationship correlated with one characteristic among a plurality of physical properties is collectively incorporated into the energy function formula as the one characteristic, and the energy function formula is simplified.

In the energy function formula, the approach to collectively incorporate a plurality of physical properties that has a relationship correlated with one characteristic among a plurality of physical properties into the energy function formula as the one characteristic, and simplify the energy function formula is not particularly limited, and can be appropriately selected depending on the intended purpose.

In an example of the technique disclosed in the present application, it is preferable to simplify the energy function formula by working out a correlation formula relating to a plurality of physical properties and replacing the plurality of physical properties with one characteristic by the worked-out correlation formula. In an example of the technique disclosed in the present application, by applying the correlation formula relating to a plurality of physical properties to the energy function formula, the plurality of physical properties may be collected into one characteristic, and the number of parameters (the number of physical properties) in the energy function formula may be decreased to simplify the energy function formula.

The approach to work out the correlation formula relating to a plurality of physical properties is not particularly limited, and can be appropriately selected depending on the intended purpose. However, an approach of working out the correlation formula based on the correlation relationship between the plurality of physical properties and a characteristic obtained by collecting the plurality of physical properties is preferable.

The approach to work out the correlation formula based on the correlation relationship between a plurality of physical properties and a characteristic obtained by collecting the plurality of physical properties is not particularly limited, and can be appropriately selected depending on the intended purpose. However, an approach using multiple regression analysis is preferable. This means that, in an example of the technique disclosed in the present application, it is preferable that one characteristic in which a plurality of physical properties is collected be derived from a plurality of physical properties that has a relationship correlated with each other among a plurality of physical properties, by the multiple regression analysis.

By deriving one characteristic in such a manner, in an example of the technique disclosed in the present application, the correlation relationship between a plurality of physical properties and a characteristic obtained by collecting the plurality of physical properties may be more precisely worked out.

The multiple regression analysis means a regression analysis that is a kind of multivariate analysis and has two or more explanatory variables, and is an analysis approach that can work out a correlation relationship between two or more explanatory variables and one objective function. In an example of the technique disclosed in the present application, for example, by performing the multiple regression analysis with a plurality of physical properties as explanatory variables and a characteristic (one characteristic) as an objective variable, a correlation formula (multiple regression formula) representing a correlation relationship between the plurality of physical properties and the one characteristic may be worked out, and the energy function formula may be simplified by the worked-out correlation formula.

In an example of the technique disclosed in the present application, in a case where multivariate analysis such as the multiple regression analysis is performed when the correlation formula is worked out, for example, it is preferable to perform the analysis based on data of a plurality of physical properties (physical property values) corresponding to a given characteristic (characteristic value). This means that, in an example of the technique disclosed in the present application, it is preferable to obtain a correlation formula representing a correlation relationship between a plurality of physical properties and one characteristic, by performing the multiple regression analysis based on data containing the value of the one characteristic and the values of the plurality of physical properties corresponding to the value of the one characteristic (giving the value of the one characteristic).

The approach to acquire data containing the value of one characteristic and the values of a plurality of physical properties corresponding to the value of the one characteristic (giving the value of the one characteristic) is not particularly limited, and can be appropriately selected depending on the intended purpose. As the approach to acquire data containing the value of one property and the values of a plurality of physical properties corresponding to the value of the one characteristic, for example, an approach of specifying, for a given mixture, substances to be mixed, the mixing percentage (composition) between these substances, and the value of each physical property in the given mixture, and working out the value of the one characteristic in the mixture for which the composition and physical properties have been specified can be mentioned.

Here, the approach to specify, for a given mixture, substances to be mixed, the mixing percentage (composition) between these substances, and the value of each physical property in the given mixture is not particularly limited, and can be appropriately selected depending on the intended purpose. For example, an approach of optimizing the performance of the mixture in terms of the calculation result using an appropriately set weighting coefficient can be mentioned. This means that, the composition and characteristics of the mixture may be specified by appropriately setting the weighting coefficient in the energy function formula and minimizing the energy function formula.

As described above, in an example of the technique disclosed in the present application, for the purpose of acquiring the data containing the value of one characteristic and the values of a plurality of physical properties corresponding to the value of the one characteristic before the calculation for optimizing the performance of the mixture, it is preferable to perform a calculation using an appropriately set weighting coefficient.

At this time, from the viewpoint of further improving the accuracy of the multiple regression analysis, it is preferable to prepare and minimize a plurality of energy function formulas in which the weighting coefficients are appropriately set, and acquire, for a plurality of mixtures, data containing the value of one characteristic and the values of a plurality of physical properties corresponding to the value of the one characteristic.

The approach to set the weighting coefficient in the energy function formula for specifying the composition of a mixture used for acquiring data containing the value of one characteristic and the values of a plurality of physical properties corresponding to the value of the one characteristic is not particularly limited, and can be appropriately selected depending on the intended purpose. For such a weighting coefficient of the energy function formula, for example, it is preferable to prepare, for each physical property included in the energy function formula, a plurality of combinations of weighting coefficients that emphasizes each physical property, and set the weighting coefficients such that the maximum value and the minimum value of each physical property in calculation can be narrowed down.

When the mixture for which the performance is to be optimized is a mixed refrigerant, for example, it is preferable to perform the calculation under a plurality of conditions such as a combination of weighting coefficients that emphasizes the thermal conductivity, a combination of weighting coefficients that emphasizes the specific heat, and a combination of weighting coefficients that emphasizes the flash point and viscosity.

In an example of the technique disclosed in the present application, as described above, for a mixture used for acquiring data containing the value of one characteristic and the values of a plurality of physical properties corresponding to the value of the one characteristic, the composition of a plurality of mixtures with variations in regard to each physical property can be specified.

Furthermore, the approach to set the weighting coefficient in the energy function formula for specifying the composition of a mixture used for acquiring data containing the value of one characteristic and the values of a plurality of physical properties corresponding to the value of the one characteristic may be, for example, an approach of automatically varying the weighting coefficient using a random number.

As the approach to work out the value of one characteristic in a mixture whose composition has been specified as described above, for example, an approach of working out the value by performing a simulation (numerical calculation) on the mixture, and an approach of working out the value by conducting an experiment on the mixture, and the like can be mentioned.

The approach to perform a simulation on the mixture whose composition has been specified is not particularly limited, and can be appropriately selected depending on the intended purpose. A known simulation approach can be used depending on the type of one characteristic to be worked out.

In an example of the technique disclosed in the present application, when the thermal resistance is used as one characteristic in a case where the mixture for which the performance is to be optimized is a mixed refrigerant, for example, the cooling performance of the cooling system that uses the mixed refrigerant is evaluated by performing a thermal fluid simulation.

Here, as described above, the thermal conductivity and the specific heat of the mixed refrigerant are deemed to correlate with the cooling performance of the cooling system that uses the mixed refrigerant. Furthermore, when examined from another aspect, the cooling performance in the cooling system can be represented by the thermal resistance. Therefore, by performing a thermal fluid simulation to acquire the temperature data in the cooling system that uses the mixed refrigerant and work out, as the cooling performance, the thermal resistance when the mixed refrigerant is used, the relationship between the thermal resistance as one characteristic, and the thermal conductivity and specific heat as a plurality of physical properties can be specified for the mixed refrigerant.

In addition, the approach to work out the value of one characteristic in a mixture whose composition has been specified by conducting an experiment on the mixture is not particularly limited, and can be appropriately selected depending on the intended purpose. For example, an approach of actually formulating the mixture and measuring the one characteristic can be used.

In an example of the technique disclosed in the present application, a correlation formula representing a correlation relationship between a plurality of physical properties and one characteristic may be obtained in the manner described above by acquiring data containing the value of the one characteristic and the values of the plurality of physical properties corresponding to the value of the one characteristic and performing the multiple regression analysis based on the acquired data.

Furthermore, in the technique disclosed in the present application, when the energy function formula is simplified, the number of characteristics to be incorporated into the energy function formula is not limited to one, and a plurality of characteristics may be incorporated into the energy function formula. For example, in an example of the technique disclosed in the present application, the energy function formula simplification unit may incorporate a plurality of characteristics into the energy function formula to simplify the energy function formula.

Here, as an example, a case where a plurality of physical properties different from each other correlates with multiple characteristics, as in the examples indicated by the following three Formulas, will be examined.

$$[\text{Characteristic 1}] = \alpha_1 \cdot [\text{Physical Property 1}] + \beta_1 \cdot [\text{Physical Property 2}]$$

$$[\text{Characteristic 2}] = \gamma_1 \cdot [\text{Physical Property 3}] + \delta_1 \cdot [\text{Physical Property 4}]$$

$$[\text{Characteristic 3}] = \varepsilon_1 \cdot [\text{Physical Property 5}] + \zeta_1 \cdot [\text{Physical Property 6}]$$

Note that $\alpha_1$, $\beta_1$, $\gamma_1$, $\delta_1$, $\varepsilon_1$, and $\zeta_1$ denote weighting coefficients for the respective physical properties in the correlation formulas.

In this case, it is assumed that the original energy function formula before being simplified is represented by the following Formula.

$$E = \alpha \cdot [\text{Physical Property 1}] + \beta \cdot [\text{Physical Property 2}] + \gamma \cdot [\text{Physical Property 3}] + \delta \cdot [\text{Physical Property 4}] + \varepsilon \cdot [\text{Physical Property 5}] + \zeta \cdot [\text{Physical Property 6}] + \ldots + \text{Constraint Term}$$

Note that $\alpha$, $\beta$, $\gamma$, $\delta$, $\varepsilon$, and $\zeta$ denote weighting coefficients for the respective physical properties in the energy function formula.

At this time, when the energy function formula is simplified by incorporating the above three correlation formulas into the above energy function formula, the simplified energy function formula is given as the following Formula.

$$E = \eta \cdot [\text{Characteristic 1}] + \theta \cdot [\text{Characteristic 2}] + \lambda \cdot [\text{Characteristic 3}] + \ldots + \text{Constraint Term}$$

Here, $\eta$, $\theta$, and $\lambda$ denote weighting coefficients for the respective characteristics.

In this example, by incorporating the above three correlation formulas into the above energy function formula, the number of parameters in the energy function formula can be decreased by three.

In this manner, in an example of the technique disclosed in the present application, by incorporating a plurality of characteristics into the energy function formula, even when the original energy function formula contains more physical properties, the performance of the mixture may be optimized in terms not only of the calculation result but also of the actual performance.

Furthermore, in the above example, a case where a plurality of physical properties different from each other correlates with multiple characteristics is indicated; however, the technique disclosed in the present application is not limited to this example, and for example, one physical property may correlate with a plurality of characteristics.

Here, as another example when a plurality of characteristics is incorporated into an energy function formula, a case where one physical property correlates with a plurality of characteristics, as in the examples indicated by the following three Formulas, will be examined.

[Characteristic 1]=$\alpha_1$·[Physical Property 1]+$\beta_1$·
[Physical Property 2]+$\gamma_1$·[Physical Property 3]

[Characteristic 2]=$\delta_1$·[Physical Property 3]+$\varepsilon_1$·
[Physical Property 4]+$\zeta_1$·[Physical Property 5]

[Characteristic 3]=$\eta_1$·[Physical Property 2]+$\theta_1$·
[Physical Property 4]+$\lambda_1$·[Physical Property 5]+$\varphi_1$·[Physical Property 6]

Note that $\alpha_1$, $\beta_1$, $\gamma_1$, $\delta_1$, $\varepsilon_1$, $\zeta_1$, $\eta_1$, $\theta_1$, $\lambda_1$, and $\varphi_1$ denote weighting coefficients for the respective physical properties in the respective correlation formulas.

In this case, it is assumed that the original energy function formula before being simplified is represented by the following Formula.

E=$\alpha$·[Physical Property 1]+$\beta$·[Physical Property 2]+$\gamma$·[Physical Property 3]+$\delta$·[Physical Property 4]+$\varepsilon$·[Physical Property 5]+$\zeta$·[Physical Property 6]+ . . . +Constraint Term Note that $\alpha$, $\beta$, $\gamma$, $\delta$, $\varepsilon$, and $\zeta$ denote weighting coefficients for the respective physical properties in the energy function formula.

At this time, when the energy function formula is simplified by incorporating the above three correlation formulas into the above energy function formula, the simplified energy function formula is given as the following Formula.

E=$\mu$·[Characteristic 1]+$\nu$·[Characteristic 2]+$\rho$·[Characteristic 3]+ . . . +Constraint Term Here, $\mu$, $\nu$, and $\rho$ denote weighting coefficients for the respective characteristics.

As indicated in this example, in an example of the technique disclosed in the present application, one physical property may correlate with a plurality of characteristics when a plurality of characteristics is incorporated into the energy function formula.

For example, in the technique disclosed in the present application, among a plurality of instances of the one characteristic, at least one physical property relating to a first instance of the one characteristic among a plurality of physical properties of the mixture that has a relationship correlated with each other may be at least one physical property relating to a second instance of the one characteristic among the plurality of physical properties of the mixture that has a relationship correlated with each other.

Furthermore, in the technique disclosed in the present application, the number of times that a characteristic obtained by collecting a plurality of physical properties is incorporated into the energy function formula is not limited to one time, and the characteristic can be incorporated a plurality of times. For example, in an example of the technique disclosed in the present application, it is preferable for the energy function formula simplification unit to incorporate one characteristic into the energy function formula a plurality of times to simplify the energy function formula.

This means that, in an example of the technique disclosed in the present application, the number of physical properties of the energy function formula may be decreased each time one characteristic is incorporated into the energy function formula, and even when the energy function formula contains more physical properties, the performance of the mixture may be optimized in terms not only of the calculation result but also of the actual performance.

<Performance Optimization Unit>

In an example of the technique disclosed in the present application, the performance optimization unit optimizes the performance of the mixture by minimizing the energy function formula simplified by the energy function formula simplification unit. In an example of the technique disclosed in the present application, by minimizing the energy function formula, the combinatorial optimization problem relating to the combination in the composition of the mixture may be solved, and composition of the mixture capable of optimizing the performance may be specified.

Here, the approach to minimize the energy function formula is not particularly limited, and can be appropriately selected depending on the intended purpose. As the approach to minimize the energy function formula, an approach of converting the energy function formula into a quadratic unconstrained binary optimization (QUBO) format Ising model and minimizing the value of the energy function formula converted into the Ising model is preferable.

As the energy function formula converted into the Ising model, for example, it is preferable to use the mathematical formula represented by following mathematical formula (1). For example, in an example of the technique disclosed in the present application, it is preferable to optimize the performance of the mixture based on the energy function formula converted into the Ising model represented by following Formula (1).

[Mathematical Formula 1]

$$E = -\sum_{i,j=0} w_{ij} x_i x_j \sum_{i=0} b_i x_i \qquad \text{Formula (1)}$$

Note that, in above Formula (1), E denotes the energy function formula.

The sign $w_{ij}$ denotes a numerical value that represents an interaction between an i-th bit and a j-th bit.

The sign $x_i$ denotes a binary variable that represents that the i-th bit has 0 or 1, and the sign $x_j$ denotes a binary variable that represents that the j-th bit has 0 or 1.

The sign $b_i$ denotes a numerical value that represents a bias for the i-th bit.

Here, $w_{ij}$ in above Formula (1) can be worked out, for example, by extracting the numerical value or the like of each parameter in the energy function formula before being converted into the Ising model, for each combination of $x_i$ and $x_j$, and is usually given as a matrix.

The first term on the right side in above Formula (1) is obtained by integrating the product of the state and the weight value (weight) of two circuits for all combinations of two circuits that can be selected from all the circuits, without omission or duplication.

Furthermore, the second term on the right side in above Formula (1) is obtained by integrating the products of the respective bias values and states of all the circuits.

For example, the energy function formula can be converted into the Ising model represented by above Formula (1) by extracting the parameters of the energy function formula before being converted into the Ising model and working out $w_{ij}$ and $b_i$.

The minimization of the value of the cost function converted into the Ising model in the manner described above can be executed in a short time by, for example, implementing an annealing method (annealing) using an annealing machine or the like. For example, in an example of the technique disclosed in the present application, it is preferable that the performance optimization unit minimize the energy function formula by the annealing method. Note that the details of the annealing method using the annealing machine will be described later.

In the following, an example of the technique disclosed in the present application will be described in more detail using exemplary device configurations, flowcharts, and the like.

Figure 3:
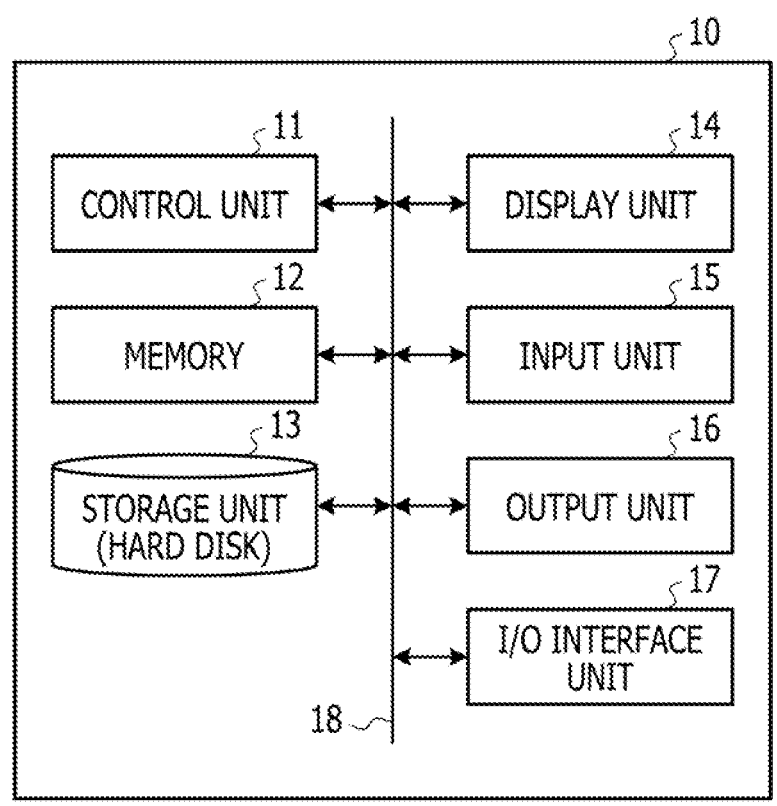
FIG. 3 is a diagram representing an exemplary configuration of a mixture performance optimization device disclosed in the present application.

FIG. 3 illustrates an exemplary hardware configuration of the mixture performance optimization device disclosed in the present application.

In the mixture performance optimization device 10, for example, a control unit 11, a memory 12, a storage unit 13, a display unit 14, an input unit 15, an output unit 16, and an input/output (I/O) interface unit 17 are connected to each other via a system bus 18.

The control unit 11 performs arithmetic operations (for example, four arithmetic operations, comparison operations, and arithmetic operations for the annealing method), hardware and software operation control, and the like.

The control unit 11 is not particularly limited, and can be appropriately selected depending on the intended purpose. For example, the control unit 11 may be a CPU or a part of an optimization device (annealing machine) used for the annealing method described later, or may be a combination of these pieces of equipment.

The energy function formula simplification unit and the performance optimization unit in the mixture performance optimization device disclosed in the present application can be achieved by, for example, the control unit 11.

The memory 12 is a memory such as a random access memory (RAM) or a read only memory (ROM). The RAM stores an operating system (OS), an application program, and the like read from the ROM and the storage unit 13, and functions as a main memory and a work area of the control unit 11.

The storage unit 13 is a device that stores various kinds of programs and data, and may be a hard disk, for example. The storage unit 13 stores a program to be executed by the control unit 11, data to be used in executing the program, an OS, and the like.

Furthermore, a mixture performance optimization program disclosed in the present application is stored in, for example, the storage unit 13, is loaded into the RAM (main memory) of the memory 12, and is executed by the control unit 11.

The display unit 14 is a display device, and may be a display device such as a cathode ray tube (CRT) monitor or a liquid crystal panel, for example.

The input unit 15 is an input device for various kinds of data, and may be a keyboard or a pointing device (such as a mouse), for example.

The output unit 16 is an output device for various kinds of data, and may be a printer, for example.

The I/O interface unit 17 is an interface for connecting various external devices.

The I/O interface unit 17 enables input and output of data on, for example, a compact disc read only memory (CD-ROM), a digital versatile disk read only memory (DVD-ROM), a magneto-optical (MO) disk, a universal serial bus (USB) memory (USB flash drive), or the like.

Figure 4:
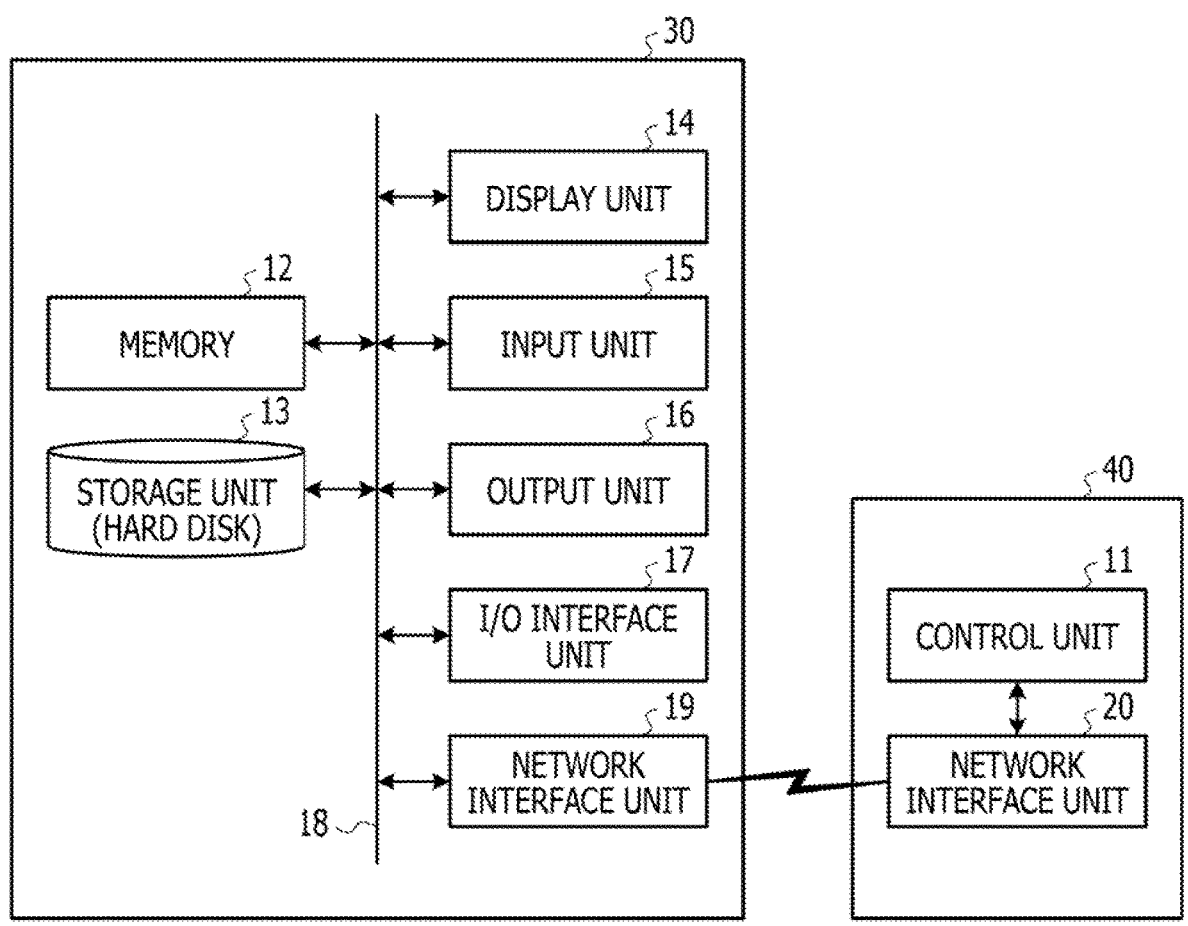
FIG. 4 is a diagram representing another exemplary configuration of the mixture performance optimization device disclosed in the present application.

FIG. 4 illustrates another exemplary hardware configuration of the mixture performance optimization device disclosed in the present application.

The example illustrated in FIG. 4 is an example of a case where the mixture performance optimization device of a cloud type is employed, and the control unit 11 is independent of the storage unit 13 and the like. In the example illustrated in FIG. 4, a computer 30 that includes the storage unit 13 and the like is connected to a computer 40 that includes the control unit 11 via network interface units 19 and 20.

The network interface units 19 and 20 are hardware that performs communication using the Internet.

Figure 5:
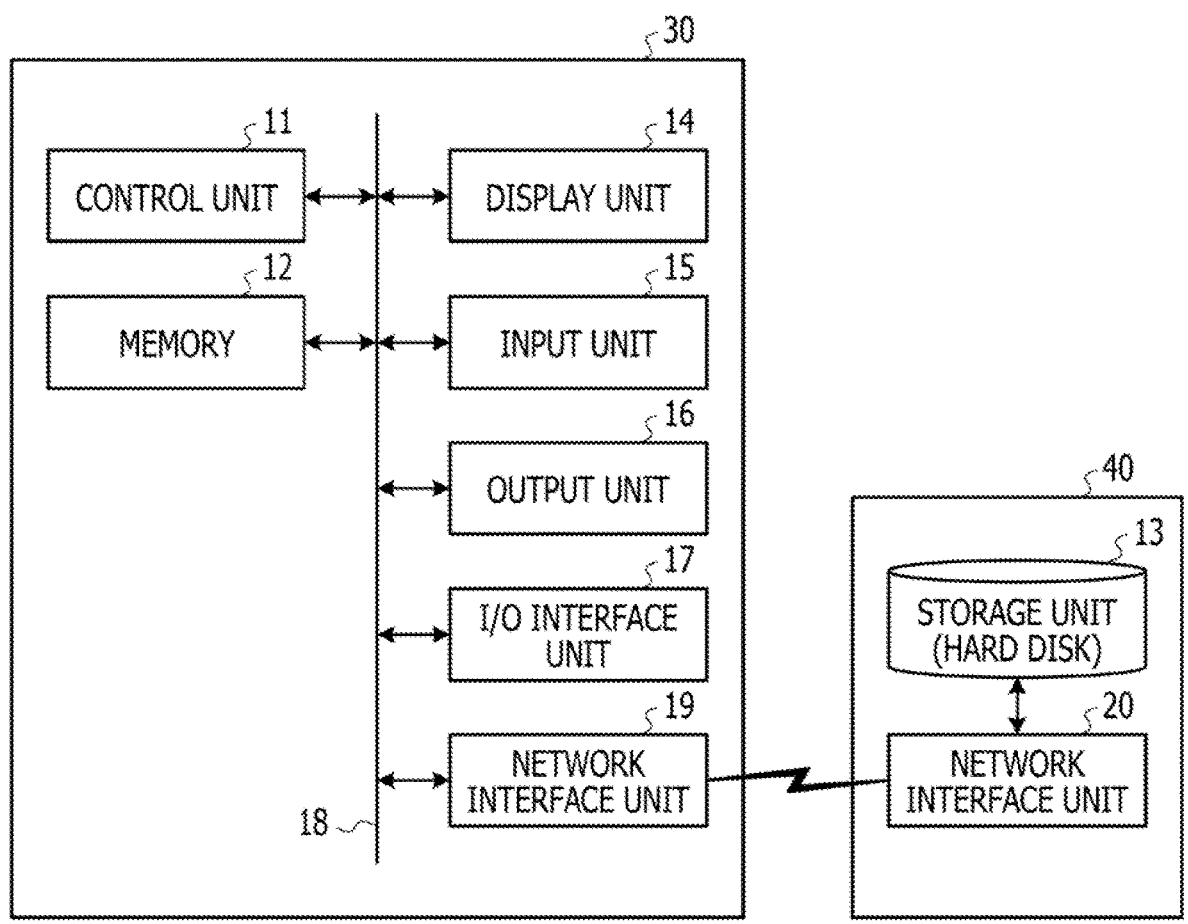
FIG. 5 is a diagram representing another exemplary configuration of the mixture performance optimization device disclosed in the present application.

FIG. 5 illustrates another exemplary hardware configuration of the mixture performance optimization device disclosed in the present application.

The example illustrated in FIG. 5 is an example of a case where the mixture performance optimization device of a cloud type is employed, and the storage unit 13 is independent of the control unit 11 and the like. In the example illustrated in FIG. 5, a computer 30 that includes the control unit 11 and the like is connected to a computer 40 that includes the storage unit 13 via network interface units 19 and 20.

Figure 6:
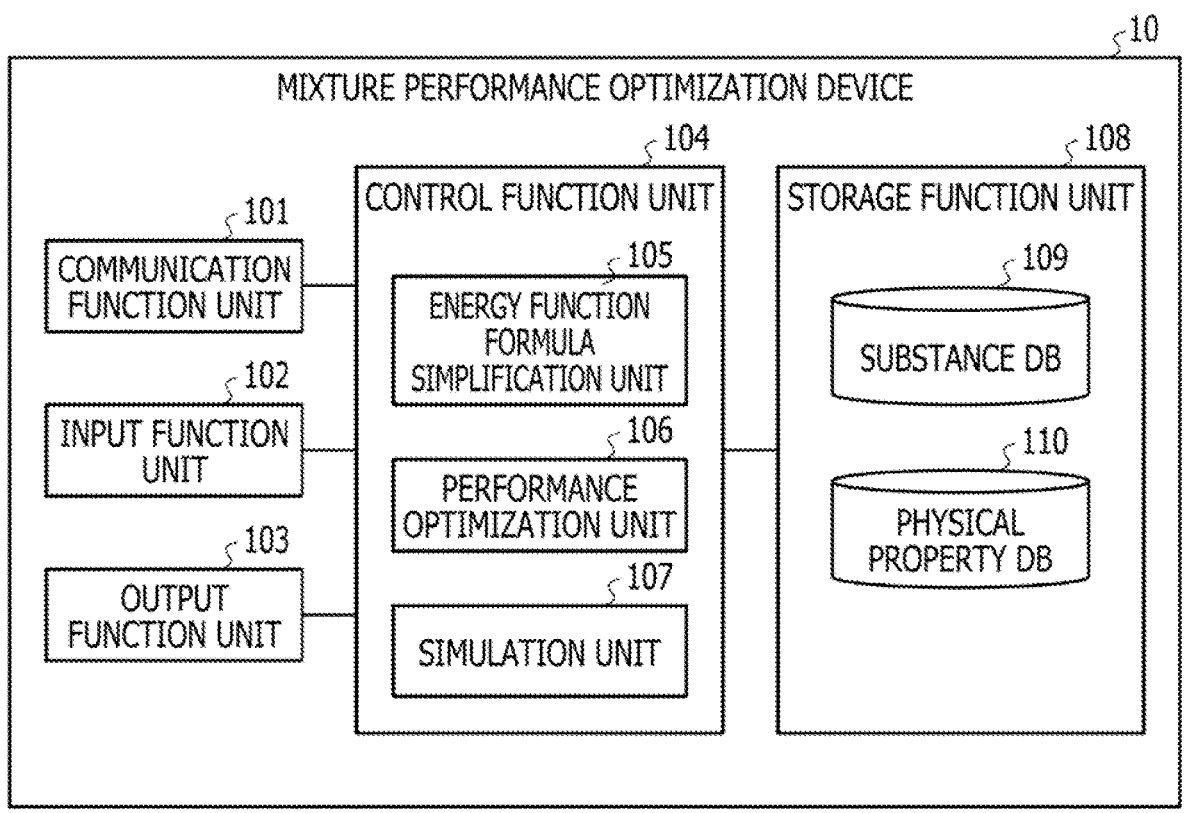
FIG. 6 is a diagram illustrating an exemplary functional configuration as an embodiment of the mixture performance optimization device disclosed in the present application.

FIG. 6 illustrates an exemplary functional configuration as an embodiment of the mixture performance optimization device disclosed in the present application.

As illustrated in FIG. 6, the mixture performance optimization device 10 includes a communication function unit 101, an input function unit 102, an output function unit 103, a control function unit 104, and a storage function unit 108.

The communication function unit 101 transmits and receives various kinds of data to and from an external device, for example. The communication function unit 101 may receive, for example, data of the bias and weight in the energy function formula converted into the Ising model, from an external device.

The input function unit 102 accepts various instructions for the mixture performance optimization device 10, for example. Furthermore, the input function unit 102 may accept, for example, inputs of data of the bias and weight in the energy function formula converted into the Ising model.

The output function unit 103 outputs the types of a plurality of substances and the mixing percentage (composition) between these substances in the mixture whose performance has been optimized, for example.

The control function unit 104 includes an energy function formula simplification unit 105, a performance optimization unit 106, and a simulation unit 107. The control function unit 104 executes various programs stored in the storage function unit 108, and also controls the operation of the entire optimization device 10, for example.

The energy function formula simplification unit 105 performs a process of simplifying the energy function formula.

The performance optimization unit 106 optimizes the performance of the mixture by minimizing the energy function formula simplified by the energy function formula simplification unit 105.

The simulation unit 107 performs a simulation (numerical calculation) on the mixture in order to work out a correlation relationship between one characteristic and a plurality of physical properties that has a relationship correlated with the one characteristic in the mixture.

The storage function unit 108 has a substance database (substance DB) 109 and a physical property database (physical property DB) 110. The storage function unit 108 stores various programs, for example.

The substance DB 109 is a database that stores information such as names and chemical formulas of substances that are candidates for the substances to be mixed into the mixture. A known compound database can be used as the substance DB 109.

The physical property DB 110 is a database that stores information on the physical properties of each substance for substances that are candidates for the substances to be mixed into the mixture. The physical property DB 110 can be obtained by collecting the physical properties (physical property values) of substances disclosed in known compound databases, chemical handbooks, academic documents, patent documents, and the like.

Here, an example of a flow for optimizing the performance of the mixture in an example corresponding to a comparative example of the technique disclosed in the present application will be described with reference to FIG. 7. Note that, in the example illustrated in FIG. 7, a case where a mixture for which the performance is to be optimized is a mixed refrigerant will be described as an example.

First, the control function unit 104 accepts an input from a user, and selects a base substance (material) in a mixed refrigerant for which the performance is to be optimized (S101). For example, when the performance of a mixed refrigerant having an insulating property is to be optimized, it is preferable to select a refrigerant material having an insulating property as a base substance.

Next, the control function unit 104 selects a plurality of candidates for the substances to be mixed into the mixed refrigerant from the substance DB 109 (S102). At this time, the control function unit 104 may select all the substances stored in the substance DB 109, or may make a selection by picking up a substance deemed to be suitable for the mixed refrigerant. Furthermore, the control function unit 104 may refer to the physical property DB 110 to select a substance for which the physical property value is stored, from the substance DB 109.

Subsequently, the control function unit 104 determines a physical property to be optimized in the mixed refrigerant (S103). For example, in S103, the control function unit 104 determines a physical property (parameter) contained in the energy function formula for performing a calculation to optimize the performance of the mixed refrigerant. In the mixed refrigerant, for example, it is preferable to select the thermal conductivity, specific heat, flash point, viscosity, electroconductivity and the like as physical properties to be optimized. Note that, in S103, the control function unit 104 preferably selects physical properties to be optimized from among the physical properties of each substance such that a physical property for which a physical property in the mixed refrigerant can be estimated is included in the physical properties to be optimized.

Following the above, the control function unit 104 acquires information on the physical properties of the candidates for the substances to be mixed, from the physical property DB 110 according to the physical properties to be optimized in the mixed refrigerant (S104). For example, in S104, the control function unit 104 refers to the physical property DB 110 for the substances selected as candidates for the substances to be mixed into the mixed refrigerant, and acquires information (physical property value) on a physical property of each substance targeted for optimization, which has been determined in S103.

Then, the control function unit 104 designates a formula capable of estimating the physical property of the mixed refrigerant from the physical properties of each substance, for the physical properties to be optimized in the mixed refrigerant (S105). For example, in S105, the control function unit 104 designates a relational expression capable of deriving a physical property in the mixed refrigerant based on the physical properties of each substance selected as a candidate for the substances to be mixed into the mixed refrigerant, based on user input and the like.

Next, the control function unit 104 defines an energy function formula including each physical property to be optimized in the mixed refrigerant (with each physical property as a parameter) (S106). For example, in S106, the control function unit 104 designates an energy function formula with each physical property to be optimized in the mixed refrigerant as a parameter, based on the formula capable of estimating the physical property in the mixed refrigerant, which has been designated in S105. Furthermore, at this time, the control function unit 104 arranges the energy function formula such that a weighting coefficient is allocated to the parameter that means each physical property, and a constraint term for searching for the composition of the mixed refrigerant is included.

For example, in S106, the control function unit 104 designates the energy function formula represented by the following Formula.

$E = \alpha \cdot [\text{Physical Property 1}] + \beta \cdot [\text{Physical Property 2}] + \gamma \cdot [\text{Physical Property 3}] + \ldots + \text{Constraint Term}$ In the Formula, E denotes the energy function formula, and $\alpha$, $\beta$, and $\gamma$ denote weighting coefficients for the respective physical properties.

Subsequently, the control function unit 104 converts the designated energy function formula into the Ising model represented by Formula (1) below (S107). For example, in S107, the control function unit 104 extracts the parameters in the designated energy function formula, and works out $b_i$ (bias) and $w_{ij}$ (weight) in following Formula (1) to convert the energy function formula into the Ising model represented by following Formula (1).

[Mathematical Formula 2]

$$E = -\sum_{i,j=0} w_{ij} x_i x_j \sum_{i=0} b_i x_i \quad \text{Formula (1)}$$

Note that, in above Formula (1), E denotes the energy function formula.

The sign $w_{ij}$ denotes a numerical value that represents an interaction between an i-th bit and a j-th bit.

The sign $x_i$ denotes a binary variable that represents that the i-th bit has 0 or 1, and the sign $x_j$ denotes a binary variable that represents that the j-th bit has 0 or 1.

The sign $b_i$ denotes a numerical value that represents a bias for the i-th bit.

Following the above, the control function unit 104 minimizes above Formula (1) using an annealing machine (S108). For example, in S108, the control function unit 104 computes the minimum energy of above Formula (1) by executing a ground state search for above Formula (1) using the annealing method, thereby locating composition of the mixed refrigerant that minimizes the energy function formula.

Then, the control function unit 104 outputs the types of substances contained in the mixed refrigerant, the mixing percentage between these substances (the composition of the mixed refrigerant), and each physical property (physical property value) of the mixed refrigerant when the energy function formula has the minimum value, based on the result of minimizing above Formula (1) (S109). Then, upon outputting the composition and physical properties of the mixed refrigerant, the control function unit 104 ends the process.

Here, in the prior art, when the performance of the mixed refrigerant is to be optimized by minimizing the energy function formula in this manner, as described earlier, even if a combination gives the minimum value to the energy function formula, in reality, the combination is not suitable as a mixed refrigerant. This means that, in the prior art, when the performance of a mixture such as a mixed refrigerant is optimized, in a case where the number of physical properties to be optimized is large, it has been difficult to optimize the energy function formula in terms not only of the calculation result but also of the actual performance, and optimum candidates for the mixture may not be sufficiently narrowed down.

Figure 7:
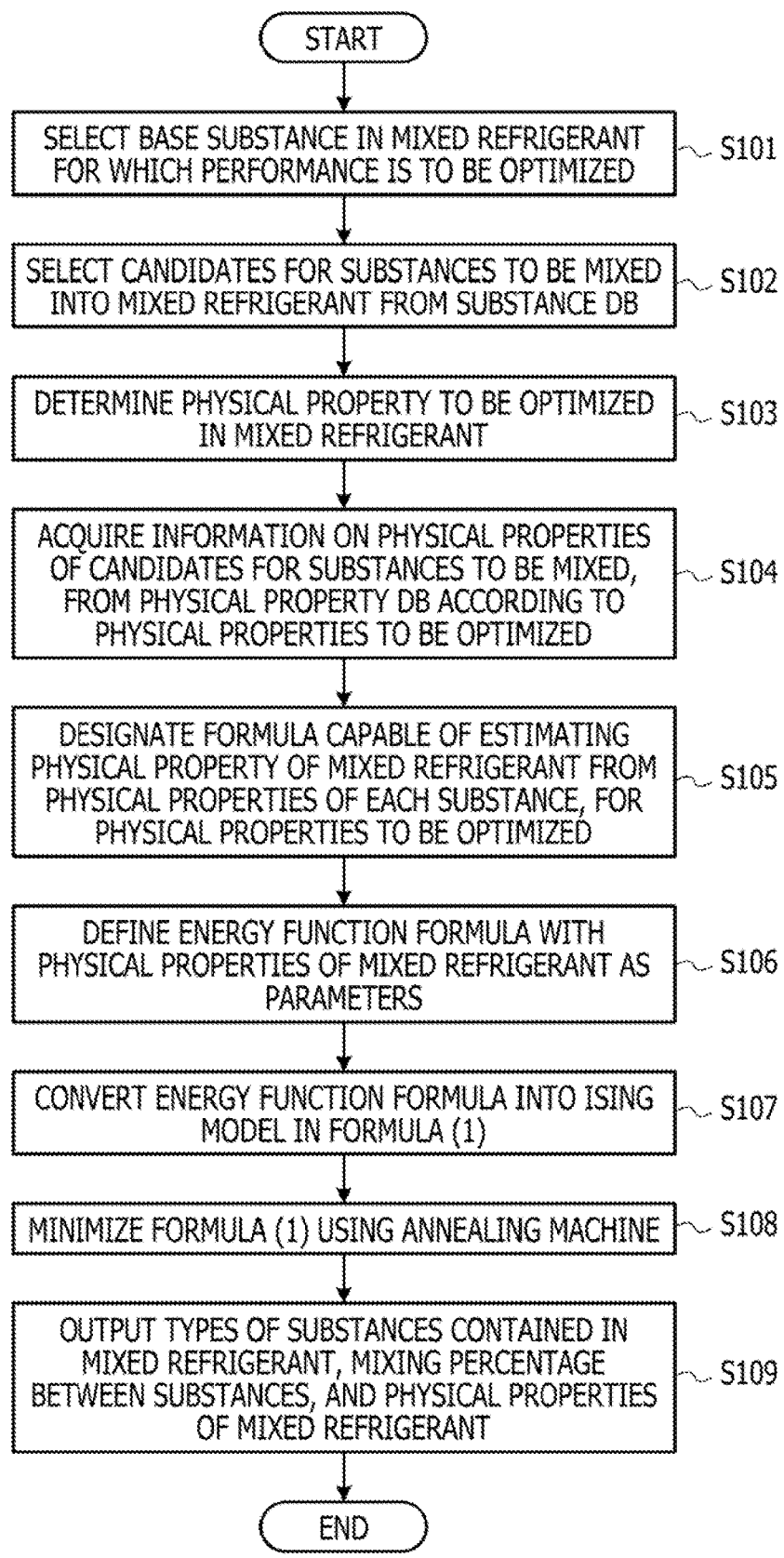
FIG. 7 is an exemplary flowchart for optimizing the performance of a mixture using an example corresponding to a comparative example of the technique disclosed in the present application.

Moreover, in the prior art, even if the calculation is performed a plurality of times in line with the flow as illustrated in FIG. 7 while the weighting coefficient in the energy function formula is appropriately changed, it has been difficult to optimize the energy function formula such that practical conditions are satisfied, and optimum candidates for the mixture may not be sufficiently narrow down.

Figure 8A:
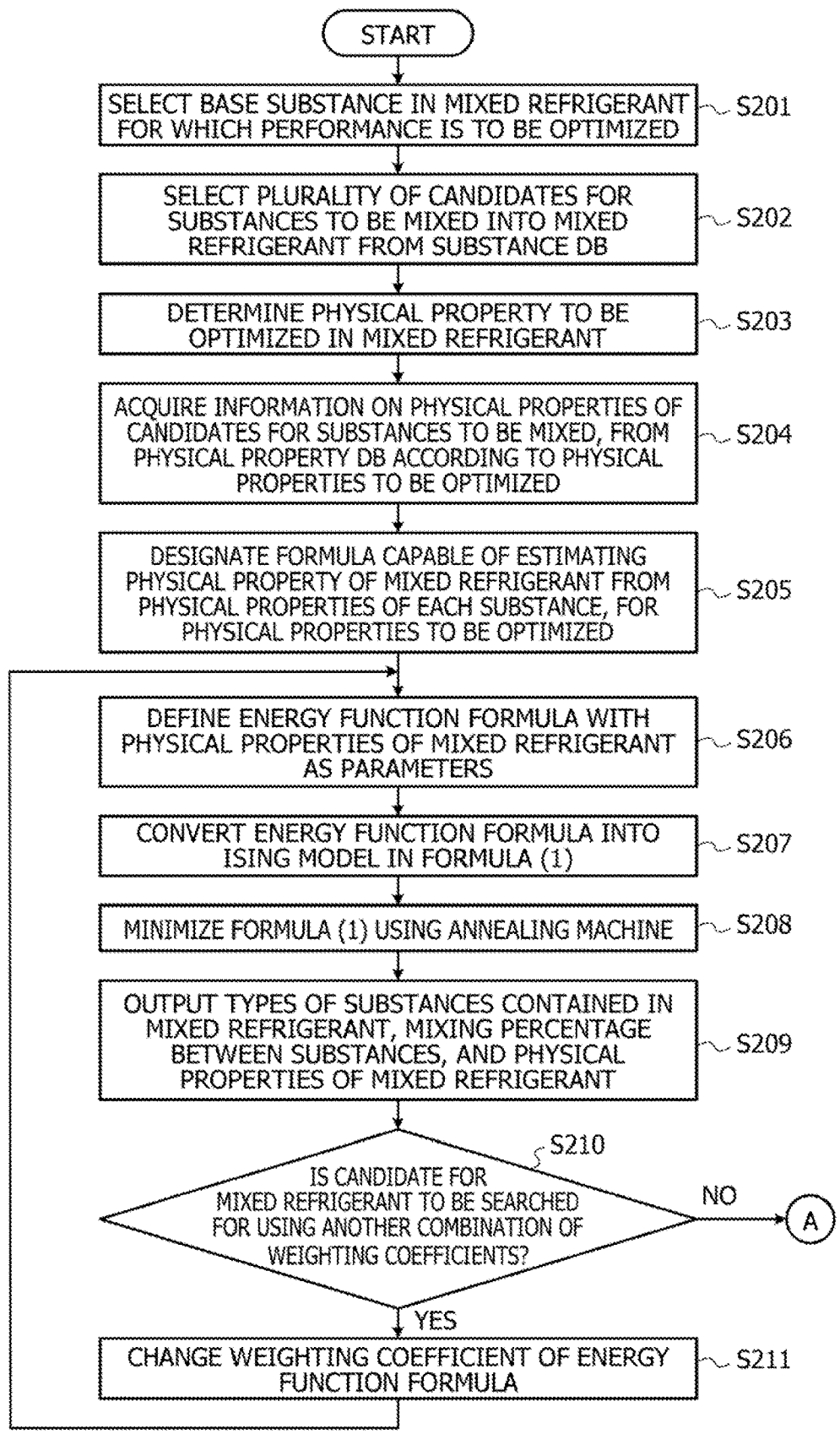
FIGS. 8A and 8B are an exemplary flowchart for optimizing the performance of a mixture using an example of the technique disclosed in the present application.
Figure 8B:
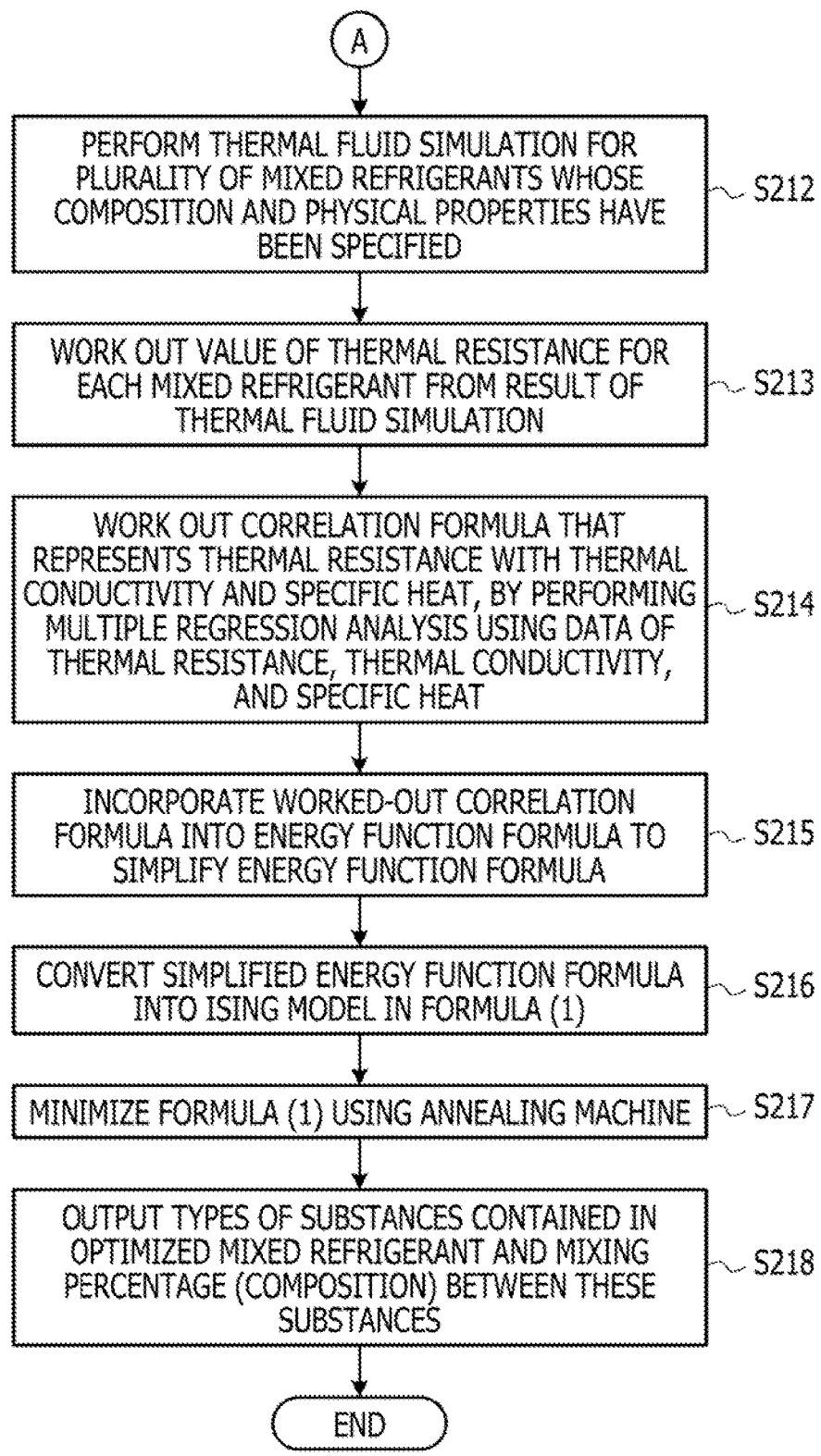

FIGS. 8A and 8B illustrates an exemplary flowchart for optimizing the performance of a mixture using an example of the technique disclosed in the present application. Furthermore, in the exemplary flowchart illustrated in FIGS. 8A and 8B, S201 to S209 can be processed in a manner similar to S101 to S109 in the exemplary flowchart illustrated in FIG. 7.

In the example in FIGS. 8A and 8B, the control function unit 104 determines whether or not to search for another candidate for the mixed refrigerant using another combination of the weighting coefficients after S209 (S210). For example, in S210, the control function unit 104 determines whether or not to further search for other composition of the mixed refrigerant depending on the number of a plurality of variations of the mixed refrigerant used in the multiple regression analysis described later.

In S210, the control function unit 104 shifts the process to S211 when searching for another candidate for the mixed refrigerant using another combination of the weighting coefficients. Furthermore, in S210, the control function unit 104 shifts the process to S212 when not searching for another candidate for the mixed refrigerant using another combination of the weighting coefficients. Note that whether or not to search for another candidate for the mixed refrigerant using another combination of the weighting coefficients may be determined, for example, by accepting a user input.

Subsequently, the simulation unit 107 in the control function unit 104 performs a thermal fluid simulation for a plurality of mixed refrigerants whose composition has been specified (S212). For example, in S212, the simulation unit 107 analyzes the performance of the cooling system when each of the mixed refrigerants is used by the thermal fluid simulation, based on the physical properties of the plurality of mixed refrigerants output in S209.

Next, the energy function formula simplification unit 105 in the control function unit 104 works out the value of the thermal resistance for each mixed refrigerant from the result of the thermal fluid simulation (S213). For example, in S213, the energy function formula simplification unit 105 works out the cooling performance of the cooling system that uses the mixed refrigerant, based on the result of the thermal fluid simulation, and calculates the value of the thermal resistance of the mixed refrigerant from the analysis result for the cooling performance of the cooling system.

Here, as described above, the thermal conductivity and the specific heat of the mixed refrigerant are deemed to correlate with the cooling performance of the cooling system that uses the mixed refrigerant. Furthermore, when examined from another aspect, the cooling performance in the cooling system can be represented by the thermal resistance when the mixed refrigerant is used in the cooling system. Therefore, the value of the thermal resistance of the mixed refrigerant may be worked out by acquiring the temperature data of the cooling system that uses the mixed refrigerant, by performing the thermal fluid simulation.

Then, the energy function formula simplification unit 105 in the control function unit 104 works out a correlation formula (multiple regression formula) that represents the thermal resistance with the thermal conductivity and the specific heat, by performing the multiple regression analysis using the data of the thermal resistance, thermal conductivity, and specific heat (S214). For example, in S214, the energy function formula simplification unit 105 uses the value of the thermal resistance calculated based on the result of the thermal fluid simulation and the values of the thermal conductivity and specific heat, which are some of the physical properties output in S209, to perform the multiple regression analysis. Then, in S214, the energy function formula simplification unit 105 works out a correlation formula that represents a correlation relationship between the thermal resistance as one characteristic and the thermal conductivity and specific heat as a plurality of physical properties.

Following the above, the energy function formula simplification unit 105 in the control function unit 104 incorporates the correlation formula worked out as described above into the energy function formula to simplify the energy function formula (S215). For example, in S215, the energy function formula simplification unit 105 incorporates the correlation formula that represents a correlation relationship between the thermal resistance as one characteristic and the thermal conductivity and specific heat as a plurality of physical properties, into the energy function formula before being converted into the Ising model, to simplify the energy function formula.

Subsequently, the performance optimization unit 106 in the control function unit 104 converts the designated energy function formula into the Ising model represented by above Formula (1) (S216). For example, in S216, the performance optimization unit 106 extracts parameters in the energy function formula and works out $b_i$ (bias) and $w_{ij}$ (weight) in above Formula (1) to convert the energy function formula into the Ising model represented by above Formula (1).

Following the above, the performance optimization unit 106 in the control function unit 104 minimizes above Formula (1) using an annealing machine (S217). For example, in S217, the performance optimization unit 106 computes the minimum energy of above Formula (1) by executing a ground state search for above Formula (1) using the annealing method, thereby locating composition of the mixed refrigerant that minimizes the energy function formula.

Then, the control function unit 104 outputs the types of substances contained in the mixed refrigerant, the mixing percentage between these substances (the composition of the mixed refrigerant), and each physical property (physical property value) of the mixed refrigerant when the energy function formula has the minimum value, based on the result of minimizing above Formula (1) (S218). Then, upon outputting the composition and physical properties of the mixed refrigerant, the control function unit 104 ends the process.

As described using the exemplary flowchart in FIGS. 8A and 8B, in an example of the technique disclosed in the present application, by collectively incorporating a plurality of physical properties that has a relationship correlated with one characteristic among a plurality of physical properties into an energy function formula as the one characteristic, the number of parameters contained in the energy function formula may be decreased. Accordingly, in an example of the technique disclosed in the present application, an appropriate weighting coefficient may be set individually for all of the parameters, and it becomes easier to optimize each physical property in the energy function formula. This means that, in an example of the technique disclosed in the present application, since it is easy to optimize each physical property in the energy function formula, when the energy function formula is minimized, each physical property may be optimized, and a mixture that has been exactly optimized in terms not only of the calculation result but also of the actual performance may be specified.

Therefore, in an example of the technique disclosed in the present application, even when the energy function formula contains many physical properties, the performance of the mixture may be optimized in terms not only of the calculation result but also of the actual performance.

Furthermore, in FIGS. 8A and 8B, the flow for optimizing the performance of the mixture has been explained in a specified order using an example of the technique disclosed in the present application; however, in the technique disclosed in the present application, the order of the respective steps can be altered as appropriate within a technically feasible range. In addition, in the technique disclosed in the present application, a plurality of steps may be comprehensively performed within a technically feasible range.

Moreover, in an example of the technique disclosed in the present application, a plurality of characteristics may be incorporated into the energy function formula by repeating S212 to S215 and other steps in the exemplary flowchart in FIGS. 8A and 8B.

Examples of the annealing method and the annealing machine will be described below.

The annealing method is a method of probabilistically working out a solution using superposition of random number values and quantum bits. The following describes a problem of minimizing a value of an evaluation function to be optimized as an example. The value of the evaluation function is referred to as energy. Furthermore, when the value of the evaluation function is maximized, the sign of the evaluation function only needs to be changed.

First, a process is started from an initial state in which one of discrete values is assigned to each variable. With respect to a current state (combination of variable values), a state dose to the current state (for example, a state in which only one variable is changed) is selected, and a state transition therebetween is considered. An energy change with respect to the state transition is calculated. Depending on the value, it is probabilistically determined whether to adopt the state transition to change the state or not to adopt the state transition to keep the original state. In a case where an adoption probability when the energy goes down is selected to be larger than that when the energy goes up, it can be expected that a state change will occur in a direction that the energy goes down on average, and that a state transition will occur to a more appropriate state over time. Then, there is a possibility that an optimum solution or an approximate solution that gives energy dose to the optimum value can be obtained finally.

If this is adopted when the energy goes down deterministically and is not adopted when the energy goes up, the energy change decreases monotonically in a broad sense with respect to time, but no further change occurs when a local solution is reached. As described above, since there are a very a large number of local solutions in the discrete optimization problem, a state is almost certainly caught in a local solution that is not so dose to an optimum value. Therefore, when the discrete optimization problem is solved, it is important to determine probabilistically whether to adopt the state.

In the annealing method, it has been proved that by determining an adoption (permissible) probability of a state transition as follows, a state reaches an optimum solution in the limit of infinite time (iteration count).

In the following, a method of working out an optimum solution using the annealing method will be described step by step.

(1) For an energy change (energy reduction) value ($-\Delta E$) due to a state transition, a permissible probability p of the state transition is determined by any one of the following functions.

[Mathematical Formula 3]

$$p(\Delta E, T) = f(-\Delta E/T) \qquad \text{Formula (1-1)}$$

[Mathematical Formula 4]

$$f_{metro}(x) = \min(1, e^x) \qquad \text{(Metropolis Method)Formula (1-2)}$$

[Mathematical Formula 5]

$$f_{metro}(x) = \min(1, e^x) \qquad \text{(Gibbs Method)Formula (1-3)}$$

Here, T denotes a parameter called a temperature value and can be changed as follows, for example.

(2) A temperature value T is logarithmically reduced with respect to an iteration count t as represented by the following Formula.

[Mathematical Formula 6]

$$T = \frac{T_0 \log(c)}{\log(t + c)} \qquad \text{Formula (2)}$$

Here, $T_0$ is an initial temperature value, and is desirably a sufficiently large value depending on a problem.

In a case where the permissible probability represented by the Formula in (1) is used, if a steady state is reached after sufficient iterations, an occupation probability of each state follows a Boltzmann distribution for a thermal equilibrium state in thermodynamics.

Then, when the temperature is gradually lowered from a high temperature, an occupation probability of a low energy state increases. Therefore, it is considered that the low energy state is obtained when the temperature is sufficiently lowered. Since this state is very similar to a state change caused when a material is annealed, this method is referred to as the annealing method (or pseudo-annealing method). Note that probabilistic occurrence of a state transition that increases energy corresponds to thermal excitation in physics.

Figure 9:
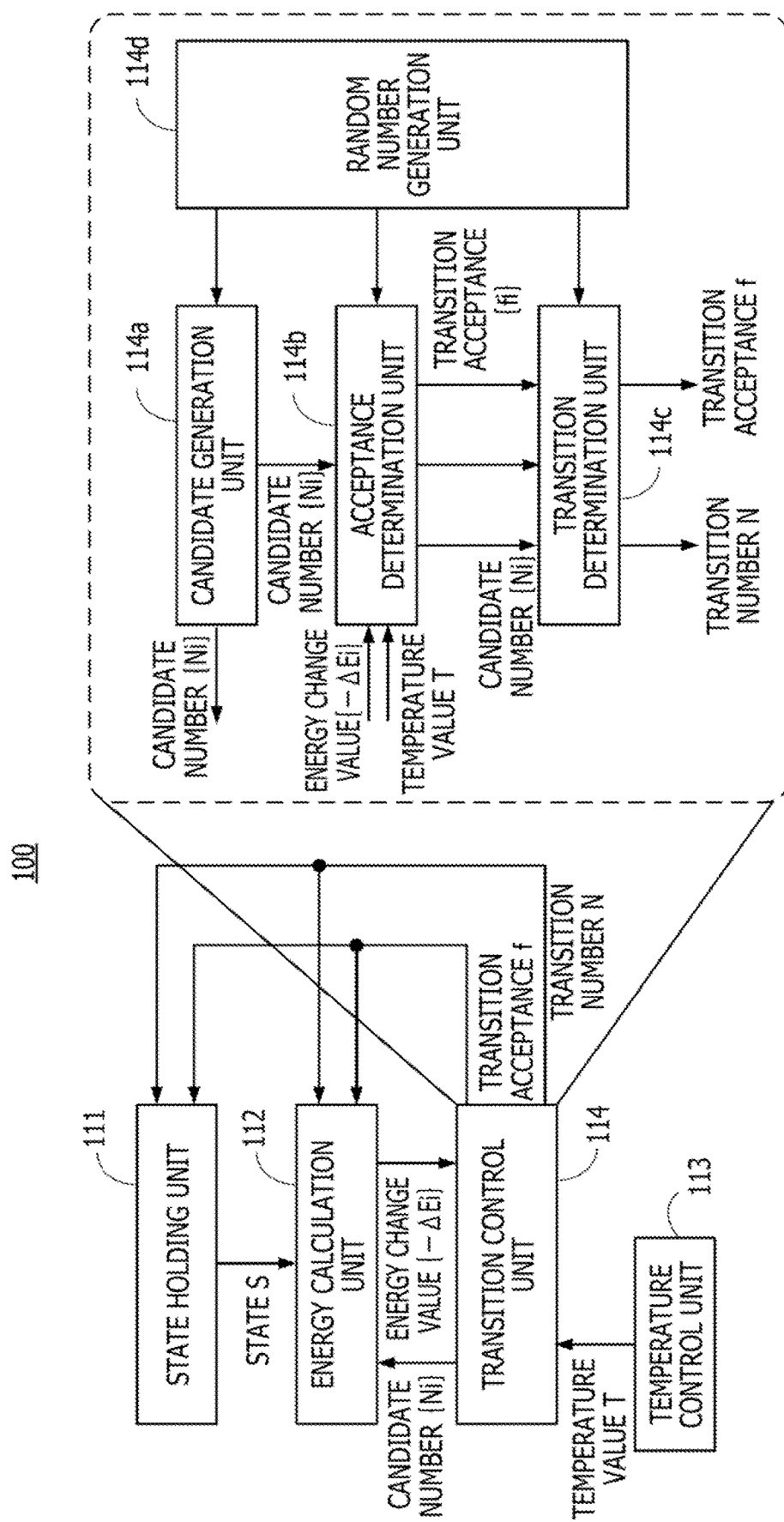
FIG. 9 is a diagram illustrating an exemplary functional configuration of an annealing machine used in an annealing method.

FIG. 9 illustrates an exemplary functional configuration of an annealing machine that implements the annealing method. However, in the following description, a case of generating a plurality of state transition candidates is also described, but a basic annealing method generates one transition candidate at a time.

An annealing machine 100 includes a state holding unit 111 that holds a current state S (a plurality of state variable values). Furthermore, the annealing machine 100 includes an energy calculation unit 112 that calculates an energy change value {−ΔEi} of each state transition when a state transition from the current state S occurs due to a change in any one of the plurality of state variable values. Moreover, the annealing machine 100 includes a temperature control unit 113 that controls the temperature value T and a transition control unit 114 that controls a state change. Note that the annealing machine 100 may be a part of the above-described mixture performance optimization device 10.

The transition control unit 114 probabilistically determines whether to accept or not any one of a plurality of state transitions according to a relative relationship between the energy change value {−ΔEi} and thermal excitation energy, based on the temperature value T, the energy change value {−ΔEi}, and a random number value.

Here, the transition control unit 114 includes a candidate generation unit 114a that generates a state transition candidate, and a propriety determination unit 114b for probabilistically determining whether or not to permit a state transition for each candidate on the basis of the energy change value {−ΔEi} and the temperature value T. Moreover, the transition control unit 114 includes a transition determination unit 114c that determines a candidate to be adopted from the candidates that have been permitted, and a random number generation unit 114d that generates a random variable.

The operation of the annealing machine 100 in one iteration is as follows.

First, the candidate generation unit 114a generates one or more state transition candidates (candidate number {Ni}) from the current state S held in the state holding unit 111 to a next state. Next, the energy calculation unit 112 calculates the energy change value {−ΔEi} for each state transition listed as a candidate using the current state S and the state transition candidates. The propriety determination unit 114b permits a state transition with a permissible probability of the Formula in above (1) according to the energy change value {−ΔEi} of each state transition using the temperature value T generated by the temperature control unit 113 and the random variable (random number value) generated by the random number generation unit 114d.

Then, the propriety determination unit 114b outputs propriety {fi} of each state transition. In a case where there is a plurality of permitted state transitions, the transition determination unit 114c randomly selects one of the permitted state transitions using a random number value. Then, the transition determination unit 114c outputs a transition number N and transition propriety f of the selected state transition. In a case where there is a permitted state transition, a state variable value stored in the state holding unit 111 is updated according to the adopted state transition.

Starting from an initial state, the above-described iteration is repeated while the temperature value is lowered by the temperature control unit 113. When a completion determination condition such as reaching a certain iteration count or energy falling below a certain value is satisfied, the operation is completed. An answer output by the annealing machine 100 is a state when the operation is completed.

The annealing machine 100 illustrated in FIG. 9 may be achieved using a semiconductor integrated circuit, for example. For example, the transition control unit 114 may include a random number generation circuit that functions as the random number generation unit 114d, a comparison circuit that functions as at least a part of the propriety determination unit 114b, a noise table described later, and the like.

Regarding the transition control unit 114 illustrated in FIG. 9, a mechanism that permits a state transition with a permissible probability represented by the Formula in (1) will be described in more detail.

A circuit that outputs 1 at a permissible probability p and outputs 0 at a permissible probability (1-p) can be achieved by inputting a uniform random number that takes the permissible probability p for input A and takes a value of an interval [0, 1) for input B in a comparator that has two inputs A and B, outputs 1 when A>B is satisfied and outputs 0 when A<B is satisfied. Therefore, if the value of the permissible probability p calculated on the basis of the energy change value and the temperature value T using the Formula in (1) is input to input A of this comparator, the above-described function can be achieved.

This means that, with a circuit that outputs 1 when f(ΔE/T) is larger than u, in which f is a function used in the Formula in (1), and u is a uniform random number that takes a value of the interval [0, 1), the above-described function can be achieved.

Furthermore, the same function as the above-described function can also be achieved by making the following modification.

Applying the same monotonically increasing function to two numbers does not change the magnitude relationship. Therefore, an output is not changed even if the same monotonically increasing function is applied to two inputs of the comparator. If an inverse function $f^{-1}$ of f is adopted as this monotonically increasing function, it can be seen that a circuit that outputs 1 when −ΔE/T is larger than $f^{-1}(u)$ can be given. Moreover, since the temperature value T is positive, it can be seen that a circuit that outputs 1 when −ΔE is larger than $Tf^{-1}(u)$ may be sufficient.

The transition control unit 114 in FIG. 9 may include a noise table that is a conversion table for achieving the inverse function $f^{-1}(u)$, and outputs a value of the following function to an input that discretizes the interval [0,1).

[Mathematical Formula 7]

$$f_{metro}^{-1}(u) = \log(u) \qquad \text{Formula (3-1)}$$

[Mathematical Formula 8]

$$f_{Gibbs}^{-1}(u) = \log\left(\frac{u}{1-u}\right) \qquad \text{Formula (3-2)}$$

Figure 10:
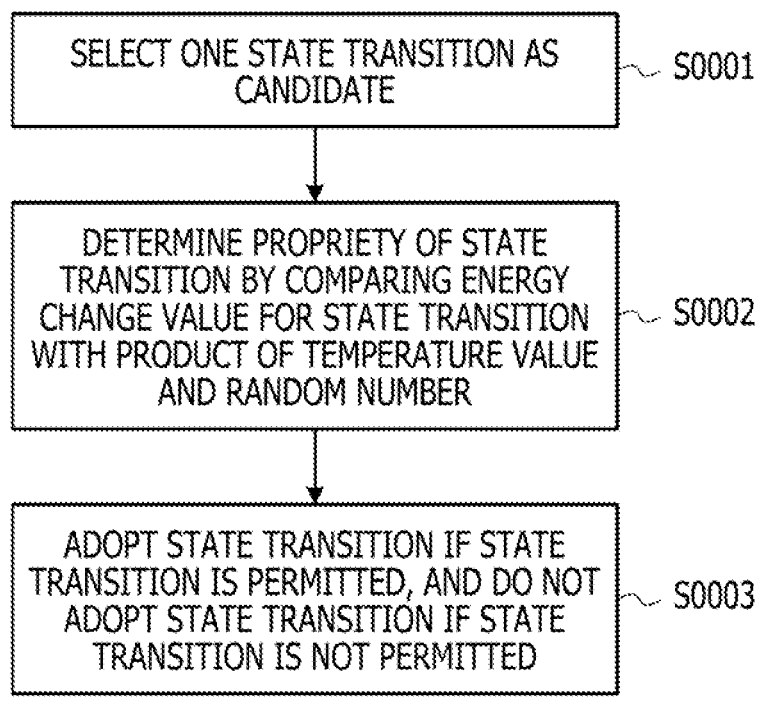
FIG. 10 is a diagram illustrating an exemplary operation flow of a transition control unit.

FIG. 10 is a diagram illustrating an exemplary operation flow of the transition control unit 114. The operation flow illustrated in FIG. 10 includes a step of selecting one state transition as a candidate (S0001), a step of determining propriety of the state transition by comparing an energy change value for the state transition with a product of a temperature value and a random number value (S0002), and a step of adopting the state transition if the state transition is permitted, and not adopting the state transition if the state transition is not permitted (S0003).

(Mixture Performance Optimization Method)

A mixture performance optimization method disclosed in the present application is a mixture performance optimization method that optimizes performance of a mixture of a plurality of substances, and includes simplifying an energy function formula that, in the energy function formula for weighting each of a plurality of physical properties in the mixture and performing a calculation to optimize the performance of the mixture, collectively incorporates a plurality of the physical properties that has a relationship correlated with one characteristic among the plurality of the physical properties into the energy function formula as the one characteristic, and simplifies the energy function formula.

The mixture performance optimization method disclosed in the present application may be implemented by, for example, the mixture performance optimization device disclosed in the present application. Furthermore, a favorable mode of the mixture performance optimization method disclosed in the present application can be made the same as the favorable mode of the mixture performance optimization device disclosed in the present application, for example.

(Optimization Program)

A mixture performance optimization program disclosed in the present application is a mixture performance optimization program that optimizes performance of a mixture of a plurality of substances, and causes a computer to perform an energy function formula simplification process of, in an energy function formula for weighting each of a plurality of physical properties in the mixture and performing a calculation to optimize the performance of the mixture, collectively incorporating a plurality of the physical properties that has a relationship correlated with one characteristic among the plurality of the physical properties into the energy function formula as the one characteristic, and simplifying the energy function formula.

The mixture performance optimization program disclosed in the present application can be configured as, for example, a program that causes a computer to execute the mixture performance optimization method disclosed in the present application. Furthermore, a favorable mode of the mixture performance optimization program disclosed in the present application can be made the same as the favorable mode of the mixture performance optimization device disclosed in the present application, for example.

The mixture performance optimization program disclosed in the present application can be created using various known programming languages according to the configuration of a computer system to be used, the type and version of the operating system, and the like.

The mixture performance optimization program disclosed in the present application may be recorded in a recording medium such as an internal hard disk or an external hard disk, or may be recorded in a recording medium such as a CD-ROM, DVD-ROM, MO disk, or USB memory.

Moreover, in a case where the mixture performance optimization program disclosed in the present application is recorded in a recording medium as mentioned above, the mixture performance optimization program can be directly used, or can be installed into a hard disk and then used through a recording medium reader included in the computer system, depending on the situation. Furthermore, the optimization program disclosed in the present application may be recorded in an external storage area (another computer or the like) accessible from the computer system through an information communication network. In this case, the mixture performance optimization program disclosed in the present application, which is recorded in an external storage area, can be used directly, or can be installed in a hard disk and then used from the external storage area through the information communication network, depending on the situation.

Note that the mixture performance optimization program disclosed in the present application may be divided for each of any processes, and recorded in a plurality of recording media.

(Computer-Readable Recording Medium)

A computer-readable recording medium disclosed in the present application records the mixture performance optimization program disclosed in the present application.

The computer-readable recording medium disclosed in the present application is not limited to any particular medium, and may be appropriately selected depending on the intended purpose. For example, the computer-readable recording medium may be an internal hard disk, an external hard disk, a CD-ROM, a DVD-ROM, an MO disk, a USB memory, or the like.

Furthermore, the computer-readable recording medium disclosed in the present application may include a plurality of recording media in which the mixture performance optimization program disclosed in the present application is recorded after being divided for each of any processes.

EXAMPLES

Hereinafter, an Example of the technique disclosed in the present application will be described, but the technique disclosed in the present application is not limited to this Example.

As an Example, the performance of a mixed refrigerant as a mixture was optimized using an example of the mixture performance optimization device disclosed in the present application. In the present Example, the performance of the mixed refrigerant was optimized in line with the flow illustrated in the flowchart in FIGS. 8A and 8B using an optimization device having the functional configuration as illustrated in FIG. 6. Furthermore, the Digital Annealer (registered trademark) was used to minimize the energy function formula (minimize the Ising model in Formula (1)).

In the present Example, as a fluorine-based refrigerant on which the mixed refrigerant is based, "Opteon SF-10 (manufactured by Chemours-Mitsui Fluoroproducts Co., Ltd.)", which is a hydrofluoroolefin (HFO) refrigerant with a low global warming potential (GWP), was selected. Note that the compound name of Opteon SF-10 is methoxyperfluoroheptene ($C_7F_{13}OCH_3$).

Five physical properties, namely, the thermal conductivity, flash point, specific heat, viscosity, and electrical conductivity, were employed as physical properties to be optimized in the mixed refrigerant. For candidates for substances (materials) to be mixed into the mixed refrigerant, the list of organic solvents in a chemical handbook was referred to, and 38 types of substances (solvent materials) whose physical property values of the above five physical properties are known were chosen and listed to form a database.

Furthermore, a relational expression that can estimate the physical properties of the mixed refrigerant is designated based on each physical property of the candidates for the substances (materials) to be mixed. For the estimation of the flash point, specific heat, and electroconductivity of the mixed refrigerant, the molar average value in mixing (a value obtained by weighting and averaging the physical property values of the respective substances based on the molar concentration of each substance to be mixed) was used.

The thermal conductivity and viscosity of the mixed refrigerant were estimated using the physical property estimation formula indicated below with reference to "Prediction Method for Physical Properties (OHE, Shuzo; Data Book Shuppansha)".

First, the thermal conductivity ($\lambda_{Lm}$) of the mixed refrigerant can be represented by the following Formula.

[Mathematical Formula 9]

$$\lambda_{l,m} = \sum_{i=1}^{N}\sum_{j=1}^{N} \phi_i \phi_j \lambda_{l,i,j} \quad (1)$$

Here, "$\lambda_{Lij}$" and "$\varphi_i$" in above Formula (1) are represented by the following two Formulas.

[Mathematical Formula 10]

$$\lambda_{l,i,j} = 2\left(\frac{1}{\lambda_{l,i}} + \frac{1}{\lambda_{l,j}}\right)^{-1} \quad (2)$$

[Mathematical Formula 11]

$$\phi_i = \frac{x_i V_i}{\sum_{j=1}^{N} x_j V_j} \quad (3)$$

"$X_i$" means the mole fraction of an i-th component, "$\varphi_i$" means the volume fraction of the i-th component, and "$V_i$" means the molecular volume of the i-th component. For example, in (1) above, by assuming N=2, the thermal conductivity of a mixture of two components can be estimated as indicated by the following Formula.

[Mathematical Formula 12]

$$\lambda_{Lm}=\phi_1^2\lambda_{L1}+2\phi_1\phi_2\lambda_{12}+\phi_2^2\lambda_{L2} \quad (4)$$

Furthermore, the kinematic viscosity ($v_m$) as the viscosity of a liquid mixture of two components can be estimated by the following Formula.

[Mathematical Formula 13]

$$v_m = \phi_1 v_1 e^{\phi_2 \alpha_2} + \phi_2 v_2 e^{\phi_1 \alpha_1} \quad (5)$$

Here, "$v_i$" means the kinematic viscosity of the i-th component, "$\varphi_i$" means the volume fraction of the i-th component, and $\alpha_1$ and $\alpha_2$ are represented by the following two Formulas individually, where it is assumed that "$v_1 < v_2$" is satisfied.

[Mathematical Formula 14]

$$\alpha_1 = -1.7\ln\left(\frac{v_2}{v_1}\right) \quad (6)$$

[Mathematical Formula 15]

$$\alpha_2 = 0.27\ln\left(\frac{v_2}{v_1}\right) + \left(1.3\ln\left(\frac{v_2}{v_1}\right)\right)^{\frac{1}{2}} \quad (7)$$

Combinations of a total of 39 types of substances including Opteon SF-10 were searched for an optimum combination of substances for improving the cooling performance, by combining three substances such that Opteon SF-10 is included. The energy function formula (E(X)) for performing a calculation to optimize the performance of the mixed refrigerant is designated by the following Formula.

[Mathematical Formula 16]

$$E(X) = -\alpha \cdot \text{Thermal Conductivity Term} - \beta \cdot \text{Flash Point Term} - \gamma \cdot \text{Specific Heat Term} + \delta \cdot \text{Viscosity Term} + \varepsilon \cdot \text{Electroconductivity Term} + \text{Constraint Term} \quad (8)$$

Note that $\alpha$, $\beta$, $\gamma$, $\delta$, and $\varepsilon$ denote weighting coefficients for the respective physical properties.

As the constraint term in the above Formula in (8), a constraint term including the following four constraints was used.

The constraint that the number of types of a plurality of substances to be mixed into the mixture is a predetermined number The constraint that the total mixing percentage between a plurality of substances in the mixture is 100%

The constraint that the same substance is not selected a plurality of times as a plurality of substances to be mixed into the mixture The constraint that the mixture contains a predetermined substance In the present Example, the predetermined number in "the constraint that the number of types of a plurality of substances to be mixed into the mixture is a predetermined number" was assumed as "3", and the predetermined substance in "the constraint that the mixture contains a predetermined substance" was assumed as "Opteon SF-10".

Then, the weighting coefficients in the above Formula in (8), namely, $\alpha$, $\beta$, $\gamma$, $\delta$, and $\varepsilon$, were appropriately changed, the above Formula in (8) was converted into the Ising model in above Formula (1), and a calculation to minimize the Ising model in above Formula (1) was repeated using the Digital Annealer.

In more detail, the combination of the weighting coefficients was changed, for example, to eight types of combinations in which the weighting coefficients of $\alpha$, $\beta$, $\gamma$, $\delta$, and $\varepsilon$ are appropriately selected, such as a combination that emphasizes the thermal conductivity and a combination that emphasizes the flash point and viscosity, and the physical property values and composition of the mixed refrigerant that gives the minimum value to the Ising model in above Formula (1) were worked out for each condition. This means that, in the present Example, the weighting coefficients for various physical properties were changed to obtain a total of eight types of mixed refrigerant candidates (mixing candidates).

Subsequently, for the above eight types of mixed refrigerant candidates, a thermal fluid simulation was performed to evaluate the cooling performance of the cooling system when each mixed refrigerant was used, using the values of the physical property of each mixed refrigerant. In the thermal fluid simulation, the values of the thermal conductivity, specific heat, viscosity, and density were used as the physical properties of each mixed refrigerant. Note that, in the thermal fluid simulation, a heat receiver in contact with the heat source in the cooling system was made into a three-dimensional model (symmetric model), and the thermal conduction of the solid and the flow of the refrigerant in the heat receiver were analyzed by a finite volume method. The thermal fluid simulation software ANSYS Fluent was used for the calculation.

Figure 11:
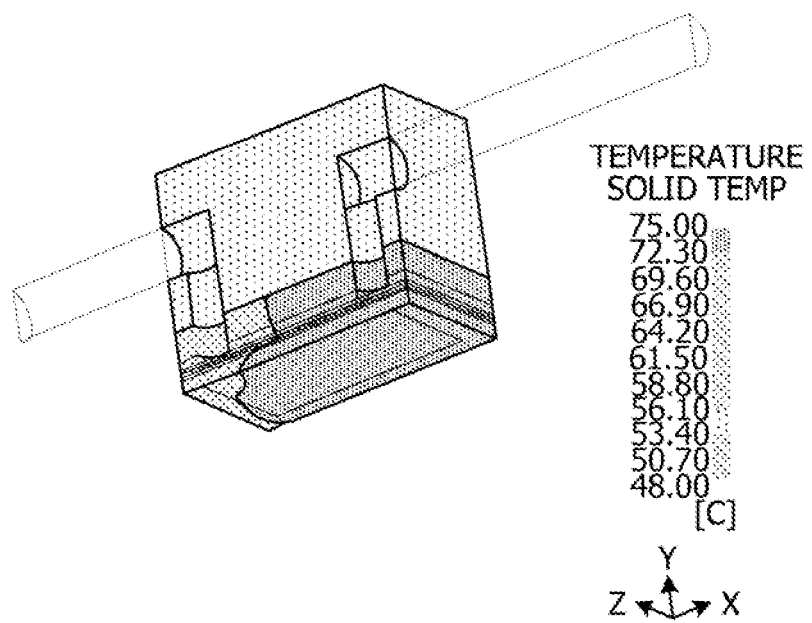
FIG. 11 is a diagram illustrating an exemplary contour diagram relating to the temperature of a heat receiver in contact with a heat source in a thermal fluid simulation in an Example.

In addition, FIG. 11 illustrates an exemplary contour diagram relating to the temperature of the heat receiver in contact with the heat source in the thermal fluid simulation. As illustrated in FIG. 11, in the thermal fluid simulation, a half (½) symmetric model obtained by cutting the heat receiver in half was used. Furthermore, the scale on the right side of FIG. 11 indicates the scale of the temperature distribution in the heat receiver. In the example illustrated in FIG. 11, the thermal fluid simulation was performed under the condition that heat was applied from the bottom portion of the heat receiver, and the mixed refrigerant flows through the groove in the cross section of the heat receiver from the left to the right in FIG. 11. Note that, in FIG. 11, the heat source (heat-generating component such as a CPU) is omitted.

Next, based on the eight individual thermal fluid simulations, data on a temperature $T_{cp}$ at the central portion of the bottom portion of the heat receiver was acquired. Then, based on the acquired temperature $T_{cp}$, the thermal resistance $R_{sys}$ in each mixed refrigerant was calculated using the following Formula.

$$R_{sys} = \frac{T_{cp} - T_{air}}{Q_{in}} \quad (9)$$

Here, "$T_{air}$" denotes the ambient temperature set in the thermal fluid simulation, and "$Q_{in}$" denotes the amount of heat input to the heat receiver.

Here, Table 1 indicates the names of the selected substances (materials) and the mixing percentage between the substances in the eight types of mixed refrigerant candidates (mixing candidates) obtained by changing the weighting coefficients for various physical properties. Table 2 indicates the thermal conductivity, specific heat, viscosity, electroconductivity, and thermal resistance. Furthermore, in Table 2, the thermal conductivity, specific heat, viscosity, and electroconductivity have physical property values calculated based on the composition of the eight mixed refrigerant candidates (mixing candidates), and the thermal resistance has a numerical value calculated based on the thermal fluid simulation.

TABLE 1

| Sub-stance No. | Substance 1 | Substance 2 | Substance 3 | Mixing Percentage (wt %) | | |
|---|---|---|---|---|---|---|
| | | | | Substance 1 | Substance 2 | Substance 3 |
| 1 | SF-10 | Diethylene Glycol Monobutyl Ether | Trans-1,2-Dichloro-ethylene | 20.6 | 73.9 | 5.5 |
| 2 | SF-10 | Dichloro-methane | Chloro-form | 31.2 | 58.5 | 10.3 |
| 3 | SF-10 | n-Pentane | Propylene Glycol | 35 | 20.9 | 44.1 |
| 4 | SF-10 | n-Pentane | Diethyl Ether | 35.2 | 7.1 | 57.7 |
| 5 | SF-10 | Propylene Glycol | Diethyl Ether | 35.1 | 7.4 | 57.5 |
| 6 | SF-10 | n-Pentane | Diethyl Ether | 35.4 | 21.1 | 43.5 |
| 7 | SF-10 | Propylene Glycol | Diethyl Ether | 35 | 14.7 | 50.3 |
| 8 | SF-10 | Dichloro-methane | Trichloro-ethylene | 30.9 | 57.9 | 11.2 |

TABLE 2

| No. | Thermal Conductivity (W/mK) | Specific Heat (J/kgK) | Viscosity (µPa · s) | Electroconductivity (S/m) | Thermal Resistance (K/W) |
|---|---|---|---|---|---|
| 1 | 1.5238 | 2016.34 | 3899.35 | 8.00E–05 | 0.718 |
| 2 | 0.1207 | 1149.2 | 574.83 | 3.64E–09 | 0.919 |
| 3 | 0.1182 | 3205.9 | 3179.88 | 6.00E–06 | 0.737 |
| 4 | 0.1157 | 2203.5 | 327.459 | 2.19E–10 | 0.762 |
| 5 | 0.1168 | 2379.3 | 473.37 | 1.00E–06 | 0.754 |
| 6 | 0.1182 | 2877.6 | 1555.85 | 5.00E–06 | 0.736 |
| 7 | 0.1167 | 2541.8 | 716.02 | 2.00E–06 | 0.748 |
| 8 | 0.1193 | 1144.5 | 573.86 | 3.62E–09 | 0.921 |

Here, as described above, among the respective physical properties of the eight mixed refrigerant candidates (mixing candidates), "thermal resistance" is deemed to be an important physical property as a refrigerant (a physical property related to the cooling performance). Accordingly, the multiple physical properties, namely, "thermal conductivity" and "specific heat", which are closely related to thermal resistance, were collected into one characteristic of "thermal resistance", by performing the multiple regression analysis. In detail, the multiple regression analysis was performed using the values of the thermal conductivity, specific heat, and thermal resistance, by employing the multiple regression formula in the format of following Formula, where y is assumed as the thermal resistance, $x_1$ is assumed as the thermal conductivity, and $x_2$ is assumed as the specific heat.

[Mathematical Formula 18]

$$y = ax_1 + bx_2 + c \quad (10)$$

As a result of the multiple regression analysis, a, b, and c in the above Formula in (10) were worked out individually as follows.

a=−0.069214632
b=−0.000100303
c=1.026848908

Then, by incorporating the above Formula in (10) in which the multiple physical properties of the thermal conductivity and specific heat have been collected into one characteristic of the thermal resistance, into the above energy function formula in (8), the above energy function formula in (8) is simplified and given as the following Formula.

[Mathematical Formula 19]

$$E(X) = -\beta \cdot \text{Flash Point Term} + \delta \cdot \text{Viscosity Term} + \varepsilon \cdot \text{Electroconductivity Term} + \eta \cdot \text{Thermal Resistance Term} + \text{Constraint Term} \quad (11)$$

Subsequently, the weighting coefficients ($\beta$, $\delta$, $\varepsilon$, and $\eta$) in the terms of the respective physical properties in above (11) were appropriately set, and the above Formula in (11) was converted into the Ising model in above Formula (1); then, the above Formula in (11) that has been converted into the Ising model in above Formula (1) was minimized using the Digital Annealer to optimize the performance of the mixed refrigerant.

When the performance of the mixed refrigerant was optimized as described above, a mixed refrigerant having the following composition was obtained as a mixed refrigerant having the physical properties and characteristics that minimize the above Formula in (11) that has been converted into the Ising model. Opteon SF-10/n-pentane/methyl alcohol=52.4/10.5/37.1 (mass %)

Figure 12:
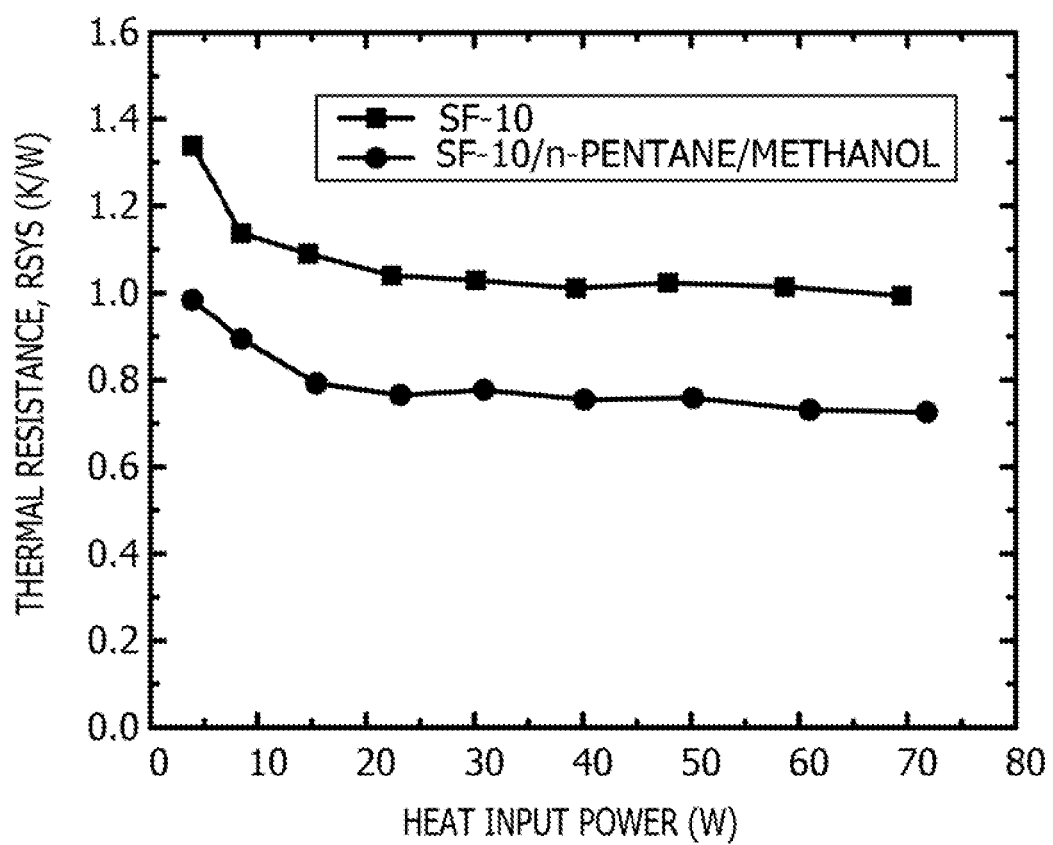
FIG. 12 is a diagram illustrating an example of a mixed refrigerant disclosed in the present application and an example of the input heat amount dependence of a thermal resistance $R_{sys}$ in a pure refrigerant using Opteon SF-10.

For this mixed refrigerant, a thermal fluid simulation for evaluating the cooling performance of the cooling system that uses this mixed refrigerant was performed in a manner similar to the above-described method. Based on the results of the thermal fluid simulation, the input heat amount dependence of the thermal resistance $R_{sys}$ was analyzed. The analysis results are illustrated in FIG. 12. In FIG. 12, the horizontal axis denotes the amount of heat input to the heat receiving portion (heat receiver), which corresponds to the amount of heat generated by the component. Furthermore, in FIG. 12, the vertical axis denotes the thermal resistance, and means that the smaller the value, the higher the cooling performance.

In addition, also for a pure refrigerant of Opteon SF-10 (a refrigerant containing 100% by mass of Opteon SF-10), a thermal fluid simulation was performed in a manner similar to the case of the above mixed refrigerant, and the input heat amount dependence of the thermal resistance $R_{sys}$ was analyzed. Comparing the mixed refrigerant specified in the present Example with the pure refrigerant of Opteon SF-10, it was confirmed that the mixed refrigerant specified in the present Example has a thermal resistance $R_{sys}$ lowered by about 24% and an improved cooling performance as compared with the pure refrigerant of Opteon SF-10.

As described above, it was ascertained that the mixed refrigerant whose performance was optimized in the present Example has a significantly lowered thermal resistance relevant to the cooling performance (a significantly improved cooling performance) as compared with the conventional refrigerant. Furthermore, the mixed refrigerant whose performance was optimized in the present Example has an insulating property, non-flammability, and low viscosity as well as high cooling performance, and is a mixed refrigerant whose actual performance as a refrigerant is optimized.

Table 3 illustrates the thermal conductivity, specific heat, viscosity, electroconductivity, and thermal resistance of the mixed refrigerant whose performance was optimized in the present Example.

TABLE 3

| | Thermal Conductivity (W/mK) | Specific Heat (J/kgK) | Viscosity (μPa · s) | Electroconductivity (S/m) | Thermal Resistance (K/W) |
|---|---|---|---|---|---|
| Mixed Refrigerant Specified in Example | 0.1254 | 2347.5 | 634.99 | 1.20E−07 | 0.745 |

Here, the above eight mixed refrigerant candidates (mixing candidates) and the mixed refrigerant whose performance was optimized in the present Example will be described in comparison with each other.

For example, the mixing candidate with "No. 1" among the mixing candidates was obtained as a result of a calculation under the condition that the weighting coefficient for the thermal conductivity term is raised (the thermal conductivity is emphasized), and has a thermal resistance of "0.718 K/W"; it can be supposed that the cooling performance is high. However, the mixing candidate with "No. 1" has a very high viscosity of "3899.35 μPa·s", and has a difficulty in flowing through a piping of the cooling system; moreover, the mixing candidate has a high electroconductivity of "8.00E-05 (8.00×10$^{-5}$) S/m and electrical conductivity, and its physical properties make it difficult to put the mixing candidate into practical use as a refrigerant. Furthermore, for example, in the mixing candidate with "No. 2", the viscosity and electroconductivity are deemed to be preferable physical properties as a refrigerant; however, the thermal resistance is "0.919 K/W", and the practical cooling performance is deemed to be very low.

As described above, the above eight mixed refrigerant candidates (mixing candidates) are combinations that give the minimum value to its respective energy function formulas, and are optimized in terms of the calculation result, but its practical performance (actual performance) as mixed refrigerants is not optimized.

On the other hand, the mixed refrigerant optimized in the present Example has a low thermal resistance of 0.745 K/W, while having an insulating property, non-flammability, and low viscosity as well as high cooling performance, and is a mixed refrigerant whose actual performance as a refrigerant is optimized. As described above, in the present Example, by simplifying the energy function formula, the performance of the mixed refrigerant was satisfactorily optimized in terms not only of the calculation result but also of the actual performance.

<Mixed Refrigerant Disclosed in Present Application>

As mentioned above, the mixed refrigerant with "Opteon SF-10 (methoxyperfluoroheptene)/n-pentane/methyl alcohol=52.4/10.5/37.1 (mass %)" has an insulating property, non-flammability, and low viscosity as well as high cooling performance, and is a mixed refrigerant whose actual performance as a refrigerant is optimized.

As described above, the mixed refrigerant disclosed in the present application contains 52% by mass of methoxyperfluoroheptene, 11% by mass of n-pentane, and 37% by mass of methyl alcohol with respect to the total amount of the mixed refrigerant. In one aspect, the mixed refrigerant disclosed in the present application has an insulating property, non-flammability, and low viscosity as well as high cooling performance, is optimized in actual performance as a refrigerant, and may be favorably used as a refrigerant.

Figure 13:
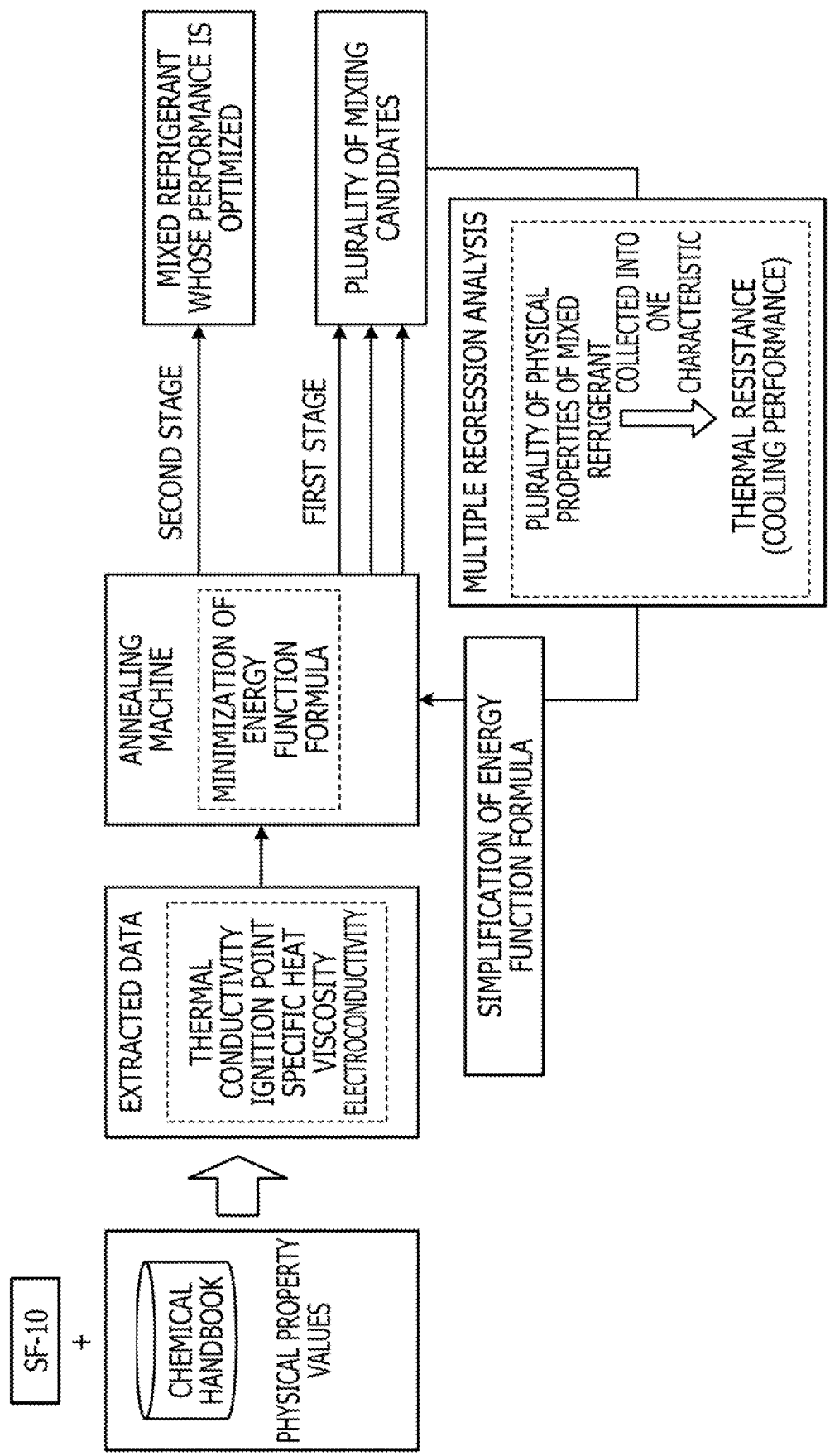
FIG. 13 is a diagram illustrating an example when the performance of a mixture is optimized in an Example of the technique disclosed in the present application.

FIG. 13 is a diagram illustrating an example when the performance of a mixture is optimized in an Example of the technique disclosed in the present application.

As illustrated in the example in FIG. 13, in the present Example, "Opteon SF-10 (manufactured by Chemours-Mitsui Fluoroproducts Co., Ltd.)" is selected as the base of a mixed refrigerant. Then, in the present Example, candidates for substances (materials) to be mixed into the mixed refrigerant and the physical property values of the candidate substances are used as a database with reference to a chemical handbook.

Subsequently, as illustrated in the example in FIG. 13, in the present Example, the physical property values of the thermal conductivity, flash point, specific heat, viscosity, and electroconductivity of the substances to be mixed into the mixed refrigerant are extracted from the database created by referring to the chemical handbook, as physical properties to be optimized.

Next, as illustrated in the example in FIG. 13, after designating a relational expression capable of estimating the physical properties of the mixed refrigerant based on each physical property of the candidates for the substances (materials) to be mixed, the weighting coefficient for each physical property is set, and the energy function formula is designated. Then, the designated energy function formula is converted into the Ising model, and the energy function formula is minimized using the Digital Annealer as an annealing machine. In the present Example, a plurality of mixed refrigerant candidates (mixing candidates) is obtained by appropriately changing the weighting coefficient for each physical property and minimizing the energy function formula a plurality of times (optimization in the first stage).

Following the above, multiple regression analysis is performed based on the values of the physical properties of the mixing candidates as a result of performing the optimization in the first stage, and a multiple regression formula that can collect a plurality of physical properties (the thermal conductivity and the specific heat in the present Example) of the mixed refrigerant into one characteristic (the thermal resistance in the present Example) is obtained. Then, in the present Example, the energy function formula is simplified by incorporating the multiple regression formula into the energy function formula.

Subsequently, in the present Example, as illustrated in the example in FIG. 13, the simplified energy function formula is converted into the Ising model, and the simplified energy function formula is minimized using the Digital Annealer as an annealing machine (optimization in the second stage). In the present Example, the performance of the mixed refrigerant may be optimized in terms not only of the calculation result but also of the actual performance of the system (device) by the second optimization, and a mixed refrigerant that has an insulating property, non-flammability, and low viscosity as well as high cooling performance and is optimized in actual performance as a refrigerant may be specified.

All examples and conditional language provided herein are intended for the pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that the various changes, substitutions, and alterations could be made hereto without departing from the spirit and scope of the invention.

What is claimed is:

1. An information processing device comprising:
   a memory; and
   a processor coupled to the memory and configured to:
   optimize performance of a mixed refrigerant which is a mixture of a plurality of substances to cool an electronic equipment;
   weight each of a plurality of physical properties in the mixture in an energy function formula for performing a calculation to optimize the performance of the mixture;
   output physical property values of the plurality of physical properties of the mixed refrigerant when the energy function formula has the minimum value;
   acquire a thermal resistance as one characteristic of the mixture by conducting an experiment or performing a simulation using the mixture;
   acquire a correlation formula between the thermal resistance and the plurality of physical properties included in the energy function formula by performing a multiple regression analysis;
   simplify the energy function formula by incorporating the correlation formula into the energy function formula;
   convert the simplified enemy function formula into an Ising model formula;
   minimize the Ising model formula using an annealing method; and
   output types and a mixing percentage of the plurality of substances of the mixed refrigerant which are obtained when the Ising model formula is minimized and has an improved cooling performance, an insulating property, non-flammability and low viscosity.

2. The information processing device according to claim 1, wherein the energy function formula is represented by the following formula:

$E=\alpha \cdot$[Physical Property 1]$+\beta \cdot$[Physical Property 2]$+\gamma \cdot$[Physical Property 3] $+ \ldots +$Constraint Term (where, the E denotes the energy function formula, and the $\alpha$, the $\beta$, and the $\gamma$ denote coefficients for the weighting).

3. The information processing device according to claim 2, wherein the constraint term includes:
   constraint that a number of types of a plurality of the substances to be mixed into the mixture is a predetermined number;
   constraint that a total mixing percentage between a plurality of the substances in the mixture is 100%;
   constraint that a same one of the substances is not selected a plurality of times as a plurality of the substances to be mixed into the mixture; and
   constraint that the mixture contains a predetermined substance among the substances.

4. The information processing device according to claim 1, wherein among the plurality of instances of the one characteristic,
   at least one physical property relating to a first instance of the one characteristic among the plurality of the physical properties of the mixture that has a relationship correlated with each other is
   at least one physical property relating to a second instance of the one characteristic among the plurality of the physical properties of the mixture that has a relationship correlated with each other.

5. The information processing device according to claim 1, wherein the processor incorporates the one characteristic into the energy function formula a plurality of times, and simplifies the energy function formula.

6. The information processing device according to claim 1, wherein the processor optimizes the performance of the mixture by minimizing the simplified energy function formula.

7. The information processing device according to claim 6, wherein the Ising model is represented by the following formula (1):

$$E = -\sum_{i,j=0} w_{ij} x_i x_j - \sum_{i=0} b_i x_i \qquad \text{Formula (1)}$$

where, in the formula (1),
the E denotes the energy function formula,
the $w_{ij}$ denotes a numerical value that represents an interaction between an i-th bit and a j-th bit,
the $b_i$ denotes a numerical value that represents a bias for the i-th bit,
the $x_i$ denotes a binary variable that represents that the i-th bit has 0 or 1, and
the $x_j$ denotes a binary variable that represents that the j-th bit has 0 or 1.

8. The information processing device according to claim 1, wherein the mixed refrigerant contains a fluorine compound.

9. The information processing device according to claim 8, wherein the fluorine compound contains a hydrofluoroolefin.

10. A non-transitory computer-readable recording medium having stored therein a mixture performance optimization program that optimizes performance of a mixed refrigerant which is a mixture of a plurality of substances to cool an electronic equipment, the mixture performance optimization program causing a computer to perform an energy function formula simplification process comprising:
- weighting each of a plurality of physical properties in the mixture in an energy function formula for performing a calculation to optimize the performance of the mixture;
- outputting physical property values of the plurality of physical properties of the mixed refrigerant when the energy function formula has the minimum value;
- acquiring a thermal resistance as one characteristic of the mixture by conducting an experiment or performing a simulation using the mixture;
- acquiring a correlation formula between the thermal resistance and the plurality of physical properties included in the energy function formula by performing a multiple regression analysis;
- simplifying the energy function formula by incorporating the correlation formula into the energy function formula;
- converting the simplified enemy function formula into an Ising model formula;
- minimizing the Ising model formula using an annealing method; and
- outputting types and a mixing percentage of the plurality of substances of the mixed refrigerant which are obtained when the Ising model formula is minimized and has an improved cooling performance, an insulating property, non-flammability and low viscosity.

11. A mixture performance optimization method that optimizes performance of a mixed refrigerant which is a mixture of a plurality of substances to cool an electronic equipment, the mixture performance optimization method comprising simplifying an energy function formula that:
- weights each of a plurality of physical properties in the mixture in an energy function formula for performing a calculation to optimize the performance of the mixture;
- outputs physical property values of the plurality of physical properties of the mixed refrigerant when the energy function formula has the minimum value;
  - acquires a thermal resistance as one characteristic of the mixture by conducting an experiment or performing a simulation using the mixture;
  - acquires a correlation formula between the thermal resistance and the plurality of physical properties included in the energy function formula by performing a multiple regression analysis;
- simplifies the energy function formula by incorporating the correlation formula into the energy function formula;
- converts the simplified energy function formula into an Ising model formula;
- minimizes the Ising model formula using an annealing method; and
- outputs types and a mixing percentage of the plurality of substances of the mixed refrigerant which are obtained when the Ising model formula is minimized and has an improved cooling performance, an insulating property, non-flammability and low viscosity.

* * * * *